US012703717B2

(12) United States Patent
Bothe et al.

(10) Patent No.: US 12,703,717 B2
(45) Date of Patent: Aug. 11, 2026

(54) FORMS OF ANTIVIRAL NUCLEOSIDES

(71) Applicants: Emory University, Atlanta, GA (US); Merck Sharp & Dohme, LLC, Rahway, NJ (US)

(72) Inventors: Jameson R. Bothe, Rahway, NJ (US); Andrew Patrick Jude Brunskill, Rahway, NJ (US); Mark Lockwood, Johns Creek, GA (US); Justin Allen Newman, Rahway, NJ (US); Manohar T. Saindane, Decatur, GA (US)

(73) Assignees: Emory University, Atlanta, GA (US); Merck Sharp & Dohme, LLC, Rahway, NJ (US)

( * ) Notice: Subject to any disclaimer, the term of this patent is extended or adjusted under 35 U.S.C. 154(b) by 369 days.

(21) Appl. No.: 18/042,982

(22) PCT Filed: Aug. 27, 2021

(86) PCT No.: PCT/US2021/048054
§ 371 (c)(1),
(2) Date: Feb. 24, 2023

(87) PCT Pub. No.: WO2022/047229
PCT Pub. Date: Mar. 3, 2022

(65) Prior Publication Data

US 2024/0025938 A1 Jan. 25, 2024

Related U.S. Application Data

(60) Provisional application No. 63/160,259, filed on Mar. 12, 2021, provisional application No. 63/071,132, filed on Aug. 27, 2020.

(51) Int. Cl.
*C07H 19/067* (2006.01)
*A61K 9/20* (2006.01)

(52) U.S. Cl.
CPC ......... *C07H 19/067* (2013.01); *A61K 9/2013* (2013.01); *A61K 9/2018* (2013.01); *A61K 9/2054* (2013.01); *C07B 2200/13* (2013.01)

(58) Field of Classification Search
USPC ........................................................... 514/49
See application file for complete search history.

(56) References Cited

U.S. PATENT DOCUMENTS

| | | | |
|---|---|---|---|
| 9,090,642 | B2 | 7/2015 | Cho et al. |
| 9,487,544 | B2 | 11/2016 | Cho et al. |
| 9,603,863 | B2 | 3/2017 | Blatt et al. |
| 9,603,864 | B2 | 3/2017 | Blatt et al. |
| 9,809,616 | B2 | 11/2017 | Amblard et al. |
| 9,815,864 | B2 | 11/2017 | Beigelman et al. |
| 9,862,743 | B2 | 1/2018 | Beigelman et al. |
| 9,877,990 | B2 | 1/2018 | Krishnan et al. |
| 10,052,342 | B2 | 8/2018 | Blatt et al. |
| 10,307,439 | B2 | 6/2019 | Blatt et al. |
| 10,370,401 | B2 | 8/2019 | Beigelman et al. |
| 2003/0008841 | A1 | 1/2003 | Devos et al. |
| 2004/0110718 | A1 | 6/2004 | Devos et al. |
| 2014/0235566 | A1 | 8/2014 | Amblard et al. |
| 2018/0244710 | A1 | 8/2018 | Yuan et al. |

FOREIGN PATENT DOCUMENTS

| | | | | |
|---|---|---|---|---|
| WO | WO 2002018404 A2 | 3/2002 | | |
| WO | WO 2002033128 A2 | 4/2002 | | |
| WO | WO 2014070771 A1 | 5/2014 | | |
| WO | WO 2015054465 A1 | 4/2015 | | |
| WO | WO 2015200205 A1 | 12/2015 | | |
| WO | WO 2017165489 A1 | 9/2017 | | |
| WO | WO-2019113462 A1 * | 6/2019 | ......... | A61K 31/7068 |
| WO | WO 2019/173602 A1 | 9/2019 | | |
| WO | 2022/133205 A1 | 6/2022 | | |

OTHER PUBLICATIONS

Third Party Submission from EP 21862867; Feb. 27, 2023 (Year: 2023).*

Mino R. Caira, "Crystalline Polymorphism of Organic Compounds," Topics in Current Chemistry, vol. 198, pp. 163-208, DOI:10.1007/3-540-69178-2_5 (1998).

International Search Report and Written Opinion of the International Searching Authority in PCT/US2021/048054, 9 pages (Dec. 9, 2021).

Supplementary Partial European Search Report in EP 21862867.5, 15 pages (Dec. 4, 2024).

Agostini et al., "Small-Molecule Antiviral β-d-N4-Hydroxycytidine Inhibits a Proofreading-Intact Coronovirus with a High Genetic Barrier to Resistance," Journal of Virology, vol. 93 Issue 24, pp. 1-14 (2019).

Gaurav et al., "Polymerases of Coronaviruses: Structure, Function, and Inhibitors," Viral Polymerases, pp. 271-300 (2019).

Hampton, "New Flu Antiviral Candidate May Thwart Drug Resistance," JAMA, vol. 323, No. 1 pp. 17, (2020).

(Continued)

*Primary Examiner* — Traviss C Mcintosh, III

(74) *Attorney, Agent, or Firm* — Finnegan, Henderson, Farabow, Garrett & Dunner LLP

(57) ABSTRACT

Novel crystalline forms of molnupiravir, including crystalline Forms I and II, which are crystalline forms of uridine 4-oxime 5'-(2-methylpropanoate), may be useful as antiviral agents, specifically as antiviral treatments for infections caused by Eastern Equine Encephalitis Virus (EEEV), Western Equine Encephalitis Virus (WEEV), and Venezuelan Equine Encephalitis Virus (VEEV), Chikungunya fever virus (CHIK), Ebola virus, influenza virus, respiratory syncytial virus (RSV), Zika virus, and coronaviruses, such as Severe Acute Respiratory Syndrome Coronavirus (SARS-CoV), Middle East Respiratory Syndrome Coronavirus (MERS-CoV), and, most recently, SARS-CoV-2 (also known as 2019-nCoV).

19 Claims, 12 Drawing Sheets

(56) References Cited

OTHER PUBLICATIONS

Law et al., "Severe acute respiratory syndrome (SARS) and coronavirus disease-2019 (COVID-19): From causes to preventions in Hong Kong," International Journal of Infectious Diseases, vol. 94, pp.

Memish et al., "Middle East respiratory syndrome," Lancelot, vol. 395, pp. 1063-1077 (2020).

Rothan et al., "The epidemiology and pathogenesis of coronavirus disease (COVID-19) outbreak," Journal of Autoimmunity, vol. 109, pp. 1-4 (2020).

Sheahan et al., "An orally bioavailable broad-spectrum antiviral inhibits SARS-CoV-2 in human airway epithelial cell cultures and multiple coronaviruses in mice," Science Translational Medicine, vol. 12, pp. 1-15 (2020).

Toots, et al., "Characterization of orally efficacious influenza drug with high resistance barrier in ferrets and human airway epithelia," Science Translational Medicine, vol. 11, pp. 1-27 (2019).

Toots, et al., "Quantitative efficacy paradigms of the influenza clinical drug candidate EIDD-2801 in the ferret model," Translational Research, vol. 218, pp. 16-28 (2020).

Toots and Plemper, Next-generation direct-acting influenza therapeutics, Translational Research, pp. 33-42 (2020).

Han et al., "Polymorphs and Solvates of Molnupiravir: Crystal Structures and Solid Forms Transformation Analysis," Cryst. Growth Des., vol. 24, pp. 4758-4769 (2024).

* cited by examiner 3500
3500
3000
2500
2000
1500
1000
500
0
INTENSITY (ARBITRARY)
ACETONE-MTBE ANTISOLVENT
STARTING MATERIAL
0 5 10 15 20 25 30 35 40 45
POSITION [°2θ] (COPPER (Cu))

30.00
26.25
22.50
18.75
15.00
11.25
7.50
3.75
0.00
-3.75
-7.50
-11.25
-15.00
-18.75
-22.50
-26.25
-30.00
HEAT FLOW (W/G)
160.43°C
95.53 J/g
162.50°C
TOLUENE
160.20°C
101.7 J/g
162.08°C
iPrOAc
160.01°C
97.32 J/g
161.32°C
MTBE
160.88°C
97.49 J/g
162.17°C
INITIAL
0
50
100
150
200
250
300
EXO UP
TEMPERATURE (°C)
UNIVERSAL V4.5A TA
INSTRUMENTS

FORMS OF ANTIVIRAL NUCLEOSIDES

This application is a national stage filing under 35 U.S.C. § 371 of International Application No. PCT/US2021/048054 filed on Aug. 27, 2021, which claims priority from U.S. Patent Application No. 63/071,132 filed Aug. 27, 2020, and U.S. Patent Application No. 63/160,259 filed Mar. 12, 2021, which are hereby incorporated by reference in their entirety.

This invention was made with government support under contract numbers HDTRA1-13-C-0072 and HDTRA1-15-C-0075, awarded by US Department of Defense, and contract numbers HHSN272201500008C and 75N93019C00058, awarded by National Institutes of Health. The government has certain rights in the invention.

The disclosure relates to novel crystalline forms of molnupiravir, which may also be disclosed as MK-4482 or EIDD-2801, as CAS Number 2349386-89-4, by its tautomers N-hydroxycytidine 5'-(2-methylpropanoate) and uridine 4-oxime 5'-(2-methylpropanoate), and/or by IUPAC names {(2R,3S,4R,5R)-3,4-dihydroxy-5-[4-(hydroxyimino)-2-oxo-3,4-dihydropyrimidin-1(2H)-yl]oxolan-2-yl}methyl 2-methylpropanoate) and {(2R,3S,4R,5R)-3,4-dihydroxy-5-[4-(hydroxyamino)-2-oxopyrimidin-1-yl]oxolan-2-yl}methyl 2-methylpropanoate), that may have antiviral activity, as well as compositions comprising the same and methods of using the same.

Viral infections, such as infections caused by Eastern Equine Encephalitis Virus (EEEV), Western Equine Encephalitis Virus (WEEV), and Venezuelan Equine Encephalitis Virus (VEEV), Chikungunya fever virus (CHIK), Ebola virus, influenza virus, respiratory syncytial virus (RSV), Zika virus, and coronaviruses, such as Severe Acute Respiratory Syndrome Coronavirus (SARS-CoV), Middle East Respiratory Syndrome Coronavirus (MERS-CoV), and, most recently, SARS-CoV-2 (also known as 2019-nCoV), continue to cause illnesses, both mild and severe to life-threatening and fatal, across the globe.

EEEV, WEEV, VEEV, and CHIK virus are vector-borne viruses (family Togaviridae, genus Alphavirus) that can be transmitted to humans through mosquito bites. The equine encephalitis viruses are CDC Category B pathogens, and the CHIK virus is Category C.

Coronaviruses cause a large percentage of respiratory illness in humans, which can be severe or life-threatening. SARS-COV-1, which emerged in 2002, has caused at least 8439 human illnesses globally and at least 812 deaths (*WHO Cumulative Number of Reported Probable Cases of SARS*, From 1 Nov. 2002 To 4 Jul. 2003, downloaded from www.who.int, on Aug. 12, 2020). Similarly, MERS-COV emerged in 2012 and has caused at least 2519 human illnesses globally and at least 866 deaths (*WHO Middle East respiratory syndrome, MERS situation update*, January 2020, downloaded from www.emro.who.int, on Aug. 12, 2020). More recently, SARS-COV-2 emerged in 2019, and it has caused at least 20, 162,474 human illnesses globally and at least 737,417 deaths (*WHO Coronavirus disease (COVID-19) Situation Report*—205, downloaded from www.who.int, on Aug. 12, 2020), as of Aug. 12, 2020, and there have been a total of 110,974,862 confirmed cases and 2,469,792 confirmed deaths worldwide as of Feb. 22, 2021 (WHO Weekly Operational Report on COVID-19, downloaded from www.who.int, on Feb. 22, 2021). SARS-COV-2, causes disease referred to a COVID-19, which can include severe respiratory disease in humans and appears to also cause neurological disease and complications that include headache, dizziness, hypogeusia, neuralgia, encephalopathy, acute cerebrovascular diseases, impaired consciousness and skeletal muscular injury (Imran Ahmad and Farooq Azam Rathore, *Neurological manifestations and complications of COVID-19: A literature review*, J. Clin. Neurosci. 77:8-12 (2020)). Additional studies are needed to further characterize the SARS-COV-2 virus and to identify ways to prevent and treat the COVID-19 disease, as well as diseases caused by other human coronaviruses.

β-D-N(4)-hydroxycytidine (NHC) was found to have anti-pestivirus and antihepacivirus activities. Antimicrob. Agents Chemother., 47(1):244-254 (2003). β-D-N(4)-hydroxycytidine, derivatives, and methods for making the same are illustrated in PCT International Patent Application No. PCT/US2015/066144, which published as PCT International Patent Application Publication No. WO2016/106050, and U.S. patent application Ser. No. 15/537,087, which published as United States Patent Application Publication No. US2019/0022116, and U.S. patent application Ser. No. 16/921,359, each of which are incorporated herein by reference in their entirety. NHC can be depicted as

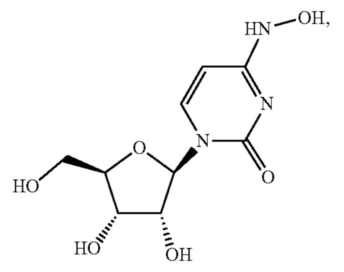 [SMILES: O=c1nc(NO)ccn1[C@@H]1O[C@H](CO)[C@@H](O)[C@H]1O]

1-((2R,3R,4S,5R)-3,4-dihydroxy-5-(hydroxymethyl)tetrahydrofuran-2-yl)-4-(hydroxyamino)pyrimidin-2(1H)-one), but, like molnupiravir, is known to tautomerize, and thus may also be described as 1-((2R,3R,4S,5R)-3,4-dihydroxy-5-(hydroxymethyl)tetrahydrofuran-2-yl)-4-(hydroxyimino)-3,4-dihydropyrimidin-2(1H)-one and depicted as:

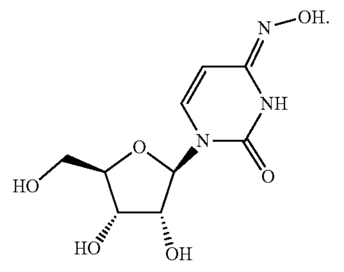 [SMILES: O=c1[nH]/c(=N\O)ccn1[C@@H]1O[C@H](CO)[C@@H](O)[C@H]1O]

In view of the potential of viral infections to cause illness and death, there remains a need for new compounds and forms that can be used to treat viral infections.

This disclosure is directed to novel crystalline forms of molnupiravir (MK-4482 or EIDD-2801), including crystalline Forms I and II, which are crystalline forms of uridine 4-oxime 5'-(2-methylpropanoate) (Compound A, also known as {(2R,3S,4R,5R)-3,4-dihydroxy-5-[4-(hydroxyimino)-2-oxo-3,4-dihydropyrimidin-1(2H)-yl]oxolan-2-yl}methyl 2-methylpropanoate):

(Compound A)

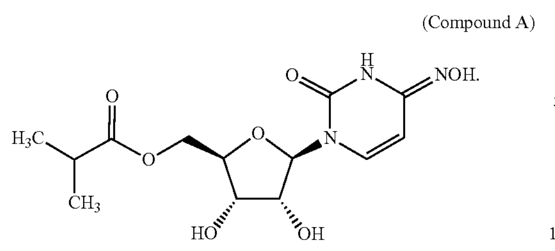

Certain crystalline forms have advantages, such as ease of processing, handling, or stability to stress. In particular, these forms may exhibit improved physicochemical properties, such as stability to stress, rendering them particularly suitable for the manufacture of various pharmaceutical dosage forms, including oral dosage forms.

The disclosure also concerns pharmaceutical compositions containing the novel forms thereof, as well as methods for using them as antiviral agents, particularly in the treatment of viral infections, such as infections caused by EEEV, WEEV, VEEV, CHIK, Ebola virus, influenza virus, RSV, Zika virus, and coronaviruses, such as SARS-CoV, MERS-CoV, and SARS-CoV-2.

DEFINITIONS

Figure 1:
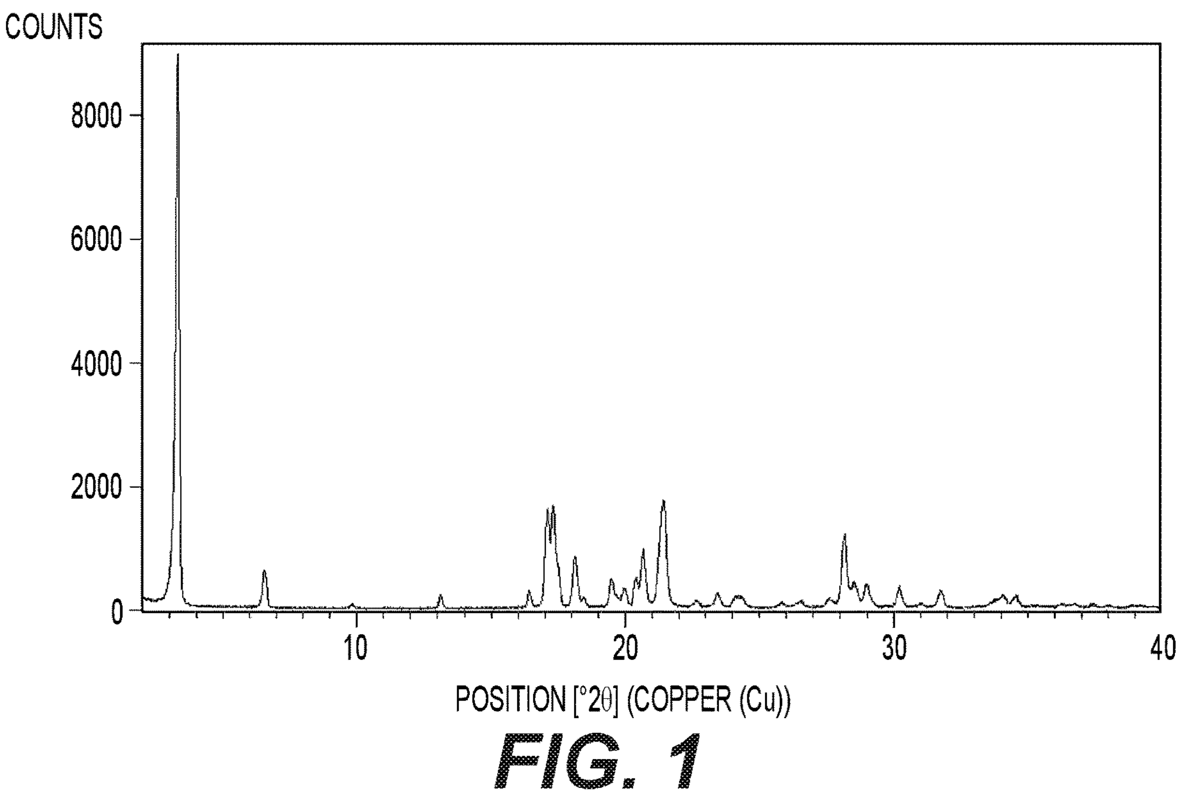
FIG. 1 depicts an X-ray powder diffraction pattern of Compound A, Form I, showing a range of 2°-40° 2θ.

Certain technical and scientific terms are specifically defined below. Unless specifically defined elsewhere in this document, all other technical and scientific terms used herein have the meaning commonly understood by one of ordinary skill in the art to which this disclosure relates. That is, terms used herein have their ordinary meaning, which is independent at each occurrence thereof. That notwithstanding and except where stated otherwise, the following definitions apply throughout the specification and claims. Chemical names, common names, and chemical structures may be used interchangeably to describe the same structure. If a chemical compound is referred to using both a chemical structure and a chemical name, and an ambiguity exists between the structure and the name, the structure predominates.

As used herein, including the appended claims, the singular forms of words such as "a," "an," and "the," include their corresponding plural references unless the context clearly dictates otherwise.

As used herein, the term "COVID-19" refers to the disease caused by SARS-CoV-2 infection. Subjects infected with SARS-CoV-2 who have developed symptoms are considered to have COVID-19.

Numerical values provided herein, and the use of the term "about", may include variations of, for example, ±0.1%, ±0.2%, ±0.3%, ±0.4%, ±0.5%, 0.75, +1%, ±2%, ±3%, ±4%, ±5%, and ±10% and their numerical equivalents. "About" when used to modify a numerically defined parameter (e.g., 2θ values of an X-ray powder diffraction pattern measured using CuKα radiation, or the chemical shift of a $^{13}C$ or $^{15}N$ as described herein) means that the parameter may vary by as much as 10% below or above the stated numerical value for that parameter; where appropriate, the stated parameter may be rounded to the nearest whole number. In addition, the term "or," as used herein, denotes alternatives that may, where appropriate, be combined; that is, the term "or" includes each listed alternative separately as well as their combination.

Exemplary methods and materials are described herein, although methods and materials similar or equivalent to those described herein can also be used in the practice or testing of the present disclosure. The materials, methods, and examples are illustrative only and not intended to be limiting.

This disclosure relates to crystalline forms, such as crystalline Forms I and II, of uridine 4-oxime 5'-(2-methylpropanoate) (Compound A, also known as {(2R,3S,4R,5R)-3,4-dihydroxy-5-[4-(hydroxyimino)-2-oxo-3,4-dihydropyrimidin-1(2H)-yl]oxolan-2-yl}methyl 2-methylpropanoate). Compound A can be depicted as:

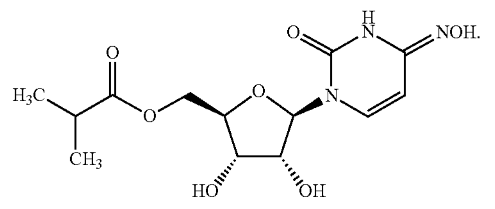

Compound A, derivatives, and methods for making the same are illustrated in PCT International Patent Application No. PCT/US2018/064503, which published as PCT International Patent Application Publication No. WO2019/113462, and in U.S. patent application Ser. No. 16/755,779, which published as United States Patent Application Publication No. US2020/0276219, each of which are incorporated herein by reference in their entirety.

Additional aspects of such embodiments provide a particular drug substance that comprises Compound A as described herein. By "drug substance" is meant the active pharmaceutical ingredient. The presence of a crystalline form in a drug substance can be detected by physical methods known to those of ordinary skill in the art, such as X-ray powder diffraction, carbon-13 cross-polarization magic-angle spinning (CPMAS) nuclear magnetic resonance (NMR) spectroscopy, and nitrogen-15 CPMAS NMR spectroscopy.

A first embodiment of the forms described herein is crystalline Form I, a crystalline form of uridine 4-oxime 5'-(2-methylpropanoate) (Compound A, Form I), which is further described below.

Aspects of this first embodiment provide uridine 4-oxime 5'-(2-methylpropanoate):

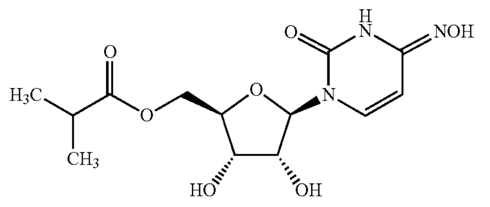

in a crystalline form having a monoclinic crystal system.

In additional aspects of this embodiment, Compound A, Form I is crystallized from a solvent system comprising a solvent chosen from ethyl acetate, MTBE, acetone, water, n-heptane, ethanol, 1-propanol, 2-propanol, acetonitrile, methanol, isopropyl acetate, 2-methyl-THF, toluene, and mixtures thereof. In additional aspects of this embodiment, Compound A, Form I is crystallized from a solvent system comprising a solvent selected from the group consisting of ethyl acetate, MTBE, acetone, water, n-heptane vapors, ethanol, 1 propanol, 2 propanol, acetonitrile, methanol, isopropyl acetate, 2 methyl-THF, toluene, and mixtures thereof. In a first instance, Compound A, Form I is crystallized from a solvent system comprising a solvent chosen from ethyl acetate, MTBE, and mixtures thereof. In some instances, Compound A, Form I is crystallized from a solvent system comprising a solvent selected from the group consisting of ethyl acetate, MTBE, and mixtures thereof. In particular, Compound A, Form I may be crystallized from a solvent system that is a mixture of ethyl acetate and MTBE. In a second instance, Compound A, Form I is crystallized from a solvent system comprising a solvent chosen from acetone, water, n-heptane, and mixtures thereof. In some instances, Compound A, Form I is crystallized from a solvent system comprising a solvent selected from the group consisting of acetone, water, n-heptane vapors, and mixtures thereof. In particular, Compound A, Form I may be crystallized from a solvent system that is a mixture of acetone and n-heptane vapors. In another instance, Compound A, Form I may be crystallized from water. In another instance, Compound A, Form I may be crystallized from acetone, water and MTBE. In another instance, Compound A, Form I may be crystallized from ethanol and water.

Additional aspects of this first embodiment of the present disclosure provides a particular drug substance that comprises at least one of the forms described herein. The presence of a particular crystalline form in a drug substance can be detected by physical methods known to those of ordinary skill in the art, such as X-ray powder diffraction (XRPD), single crystal X-ray diffraction, carbon-13 cross-polarization magic-angle spinning (CPMAS) nuclear magnetic resonance (NMR) spectroscopy, and nitrogen-15 CPMAS NMR spectroscopy.

In aspects of the first embodiment, Compound A, Form I is characterized by an X-ray powder diffraction pattern containing at least 4° 2θ values measured using CuKα radiation chosen from: about 3.34° 2θ, about 6.53° 2θ, about 13.11° 2θ, about 17.06° 2θ, about 17.33° 2θ, about 18.13° 2θ, about 19.51° 2θ, about 19.97° 2θ, and about 21.47° 2θ. In particular aspects, Compound A, Form I is characterized by having an X-ray powder diffraction pattern containing ° 2θ values measured using CuKα radiation at about 3.34° 2θ, about 19.51° 2θ, about 19.97° 2θ, and about 21.47° 2θ. In still more particular aspects, Compound A, Form I is characterized by an X-ray powder diffraction pattern containing at least 4° 2θ values measured using CuKα radiation chosen from: about 3.34° 2θ, about 6.53° 2θ, about 13.11° 2θ, about 18.13° 2θ, about 19.51° 2θ, about 19.97° 2θ, and about 21.47° 2θ. In further aspects, Compound A, Form I is characterized by having an X-ray powder diffraction pattern containing at least 5 o° 2θ values measured using CuKα radiation chosen from: about 3.34° 2θ, about 6.53° 2θ, about 13.11° 2θ, about 17.06° 2θ, about 17.33° 2θ, about 18.13° 2θ, about 19.51° 2θ, about 19.97° 2θ, and about 21.47° 2θ.

In further aspects of the first embodiment, Compound A, Form I is characterized by an X-ray powder diffraction pattern containing at least 4 t ° 2θ values measured using CuKα radiation chosen from: 3.34° 2θ±0.3° 2θ, 6.53° 2θ±0.3° 2θ, 13.11° 2θ±0.3° 2θ, 17.06° 2θ 0.3° 2θ, 17.33° 2θ±0.3° 2θ, 18.13° 2θ±0.3° 2θ, 19.51° 2θ±0.3° 2θ, 19.97° 2θ±0.3° 2θ, and 21.47° 2θ±0.3° 2θ. In particular aspects, Compound A, Form I is characterized by an X-ray powder diffraction pattern containing ° 2θ values measured using CuKα radiation at about 3.34° 2θ±0.3° 2θ, 19.51° 2θ±0.3° 2θ, 19.97° 2θ±0.3°2θ, and 21.47° 2θ±0.3°2θ. In still more particular aspects, Compound A, Form I is characterized by an X-ray powder diffraction pattern containing at least 4 of ° 2θ values measured using CuKα radiation at: 3.34°2θ±0.3° 2θ, 6.53° 2θ±0.3° 2θ, 13.11° 2θ±0.3° 2θ, 18.13° 2θ±0.3° 2θ, 19.51° 2θ±0.3° 2θ, 19.97° 2θ±0.3° 2θ, and 21.47° 2θ±0.3° 2θ. In further aspects, Compound A, Form I is characterized by an X-ray powder diffraction pattern containing at least 5 of the following ° 2θ values measured using CuKα radiation: 3.34° 2θ±0.3° 2θ, 6.53° 2θ±0.3° 2θ, 13.11° 2θ±0.3° 2θ, 17.06° 2θ±0.3° 2θ, 17.33° 2θ±0.3° 2θ, 18.13° 2θ±0.3° 2θ, 19.51° 2θ±0.3° 2θ, 19.97° 2θ±0.3° 2θ, and 21.47° 2θ±0.3° 2θ.

In still further aspects of the first embodiment, Compound A, Form I is characterized by an X-ray powder diffraction pattern containing at least 4 of the following ° 2θ values measured using CuKα radiation: 3.34° 2θ±0.2° 2θ, 6.53° 2θ±0.2° 2θ, 13.11° 2θ±0.2° 2θ, 17.06° 2θ±0.2° 2θ, 17.33° 2θ±0.2° 2θ, 18.13° 2θ±0.2° 2θ, 19.51° 2θ±0.2° 2θ, 19.97° 2θ±0.2° 2θ, and 21.47° 2θ±0.2° 2θ. In particular aspects, Compound A, Form I is characterized by an X-ray powder diffraction pattern containing the following ° 2θ values measured using CuKα radiation: about 3.34° 2θ±0.2° 2θ, 19.51° 2θ±0.2° 2θ, 19.97° 2θ0.2° 2θ, and 21.47° 2θ±0.2° 2θ. In still more particular aspects, Compound A, Form I is characterized by an X-ray powder diffraction pattern containing at least 4 of the following ° 2θ values measured using CuKα radiation: 3.34° 2θ±0.2° 2θ, 6.53° 2θ±0.2° 2θ, 13.11° 2θ±0.2° 2θ, 18.13° 2θ±0.2° 2θ, 19.51° 2θ±0.2° 2θ, 19.97° 2θ±0.2° 2θ, and 21.47° 2θ±0.2° 2θ. In further aspects, Compound A, Form I is characterized by an X-ray powder diffraction pattern containing at least 5 of the following ° 2θ values measured using CuKα radiation: 3.34° 2θ±0.2° 2θ, 6.53° 2θ±0.2° 2θ, 13.11° 2θ±0.2° 2θ, 17.06° 2θ±0.2° 2θ, 17.33° 2θ0.2° 2θ, 18.13° 2θ±0.2° 2θ, 19.51° 2θ±0.2° 2θ, 19.97° 2θ±0.2° 2θ, and 21.47° 2θ±0.2° 2θ.

A further aspect of this embodiment provides a composition comprising Compound A wherein about 100% of Compound A is in the form of Compound A, Form I. Further aspects of this embodiment include compositions comprising Compound A, wherein about 99%, about 98%, about 97%, about 96%, about 95%, about 94%, about 93%, about 92%, about 91%, about 90%, about 89%, about 88%, about 87%, about 86%, about 85%, about 84%, about 83%, about 82%, about 81%, about 80%, about 79%, about 78%, about 77%, about 76%, about 75%, about 74%, about 73%, about 72%, about 71%, about 70%, about 69%, about 68%, about 67%, about 66%, about 65%, about 64%, about 63%, about 62%, about 61%, about 60%, about 59%, about 58%, about 57%, about 56%, about 55%, about 54%, about 53%, about 52%, about 51%, about 50%, about 49%, about 48%, about 47%, about 46%, about 45%, about 44%, about 43%, about 42%, about 41%, about 40%, about 39%, about 38%, about 37%, about 36%, about 35%, about 34%, about 33%, about 32%, about 31%, about 30%, about 29%, 28%, 27%, about 26%, about 25%, about 24%, about 23%, about 22%, about 21%, about 20%, about 19%, about 18%, about 17%, about 16%, about 15%, about 14%, about 13%, about 12%, about 11%, about 10%, about 9%, about 8%, about 7%, about 6%, about 5%, about 4%, about 3%, about 2%, or about 1% of Compound A is in the form of Compound A, Form I. In a subaspect of the foregoing aspects, the balance of Compound A in the composition is in the form of Compound A, Form II. Further aspects of this embodiment include compositions comprising Compound A, wherein 99%, 98%, 97%, 96%, 95%, 94%, 93%, 92%, 91%, 90%, 89%, 88%, 87%, 86%, 85%, 84%, 83%, 82%, 8100, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, or 1% of Compound A is in the form of Compound A, Form I. In a subaspect of the foregoing, the balance of Compound A in the composition is in the form of Compound A, Form II.

In aspects of this embodiment, about 10% to about 100% of Compound A in the composition is in the form of Compound A, Form I, such as from about 25% to about 98%, from about 50% to about 96%, from about 75% to about 95%, from about 90% to about 94%, or about 92%. In certain subaspects of this aspect, the balance of Compound A in the composition is in the form of Compound A, Form II.

Still another aspect of this embodiment is Compound A, Form I of 100%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, or 1% purity.

Figure 2:
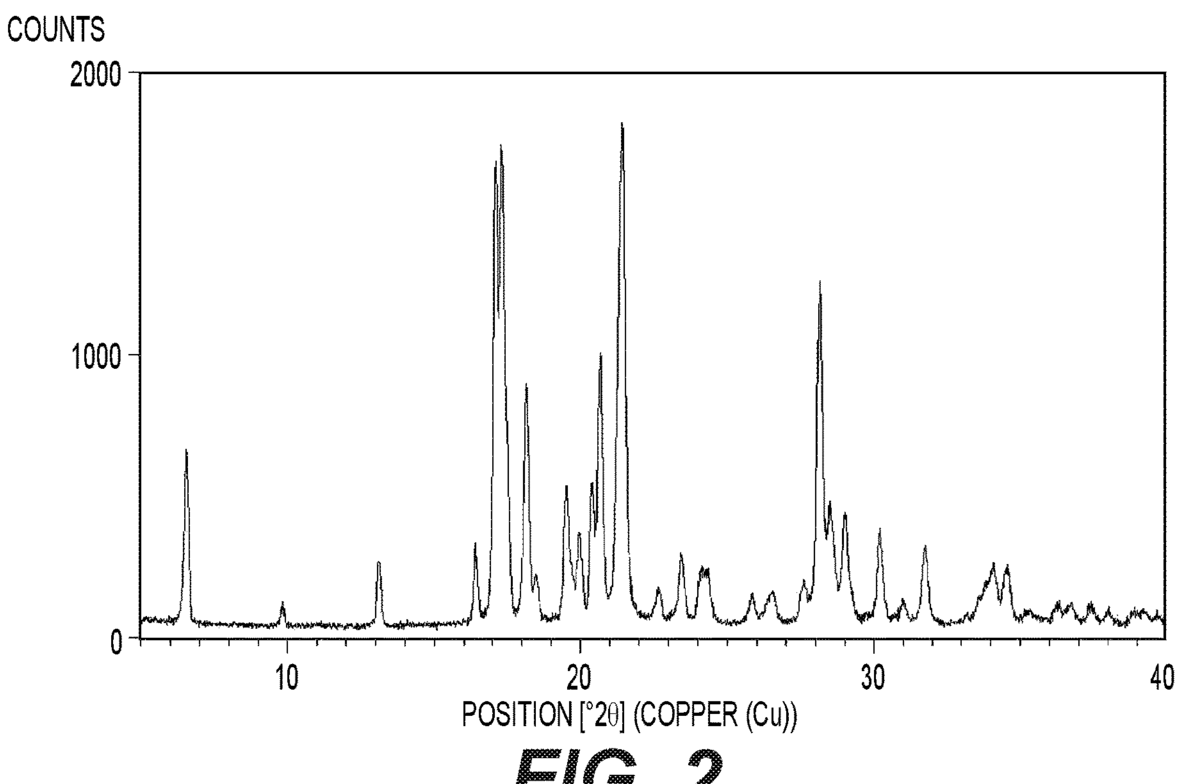
FIG. 2 depicts an X-ray powder diffraction pattern of Compound A, Form I, showing a range of 5°-40° 2θ.
Figure 12:
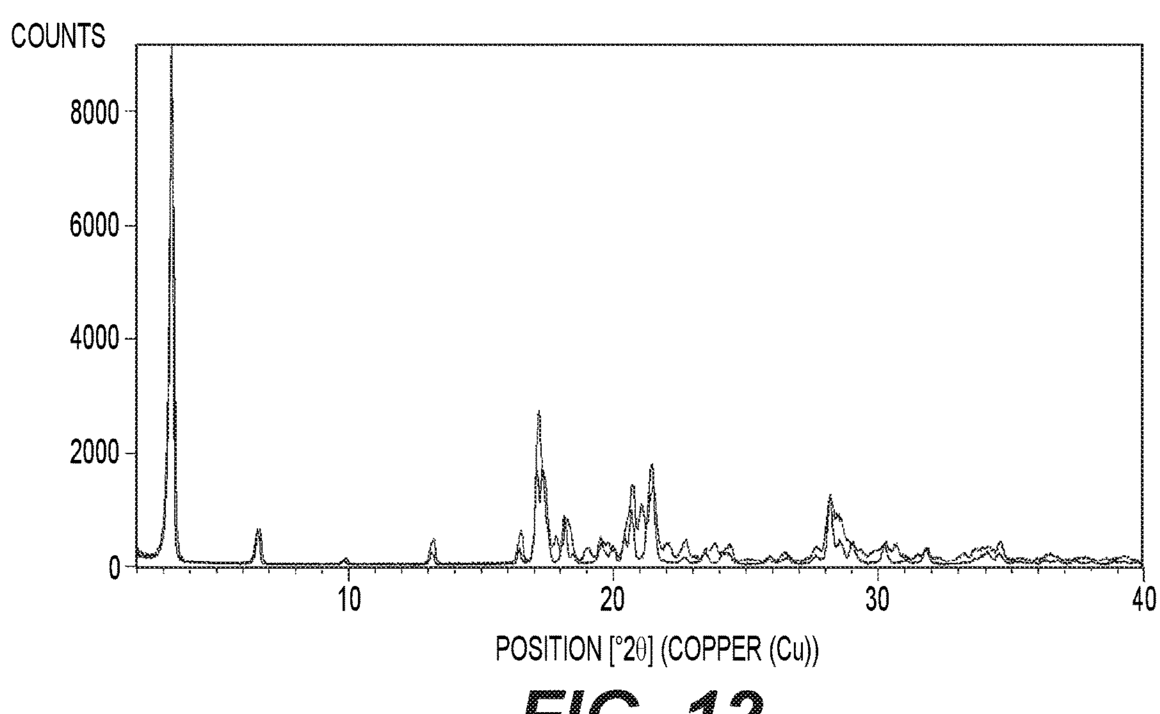
FIG. 12 depicts an overlay of X-ray powder diffraction patterns of Compound A, Form I and Compound A, Form II, showing a range of 2°-40° 2θ. The black line represents a diffractogram of Compound A, Form I, and the grey line represents a diffractogram of Compound A, Form II.
Figure 13:
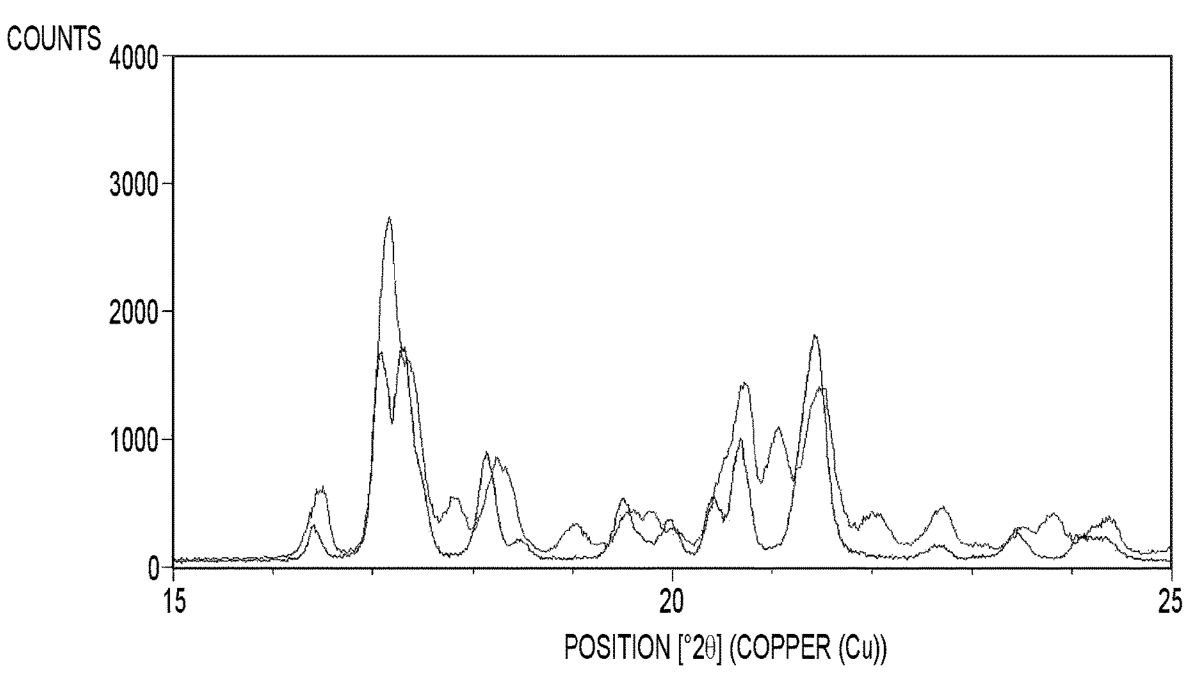
FIG. 13 depicts a range of 15°-25° 2θ of the overlaid X-ray powder diffraction patterns of Compound A, Form I and Compound A, Form II from FIG. 12. The black line represents the diffractogram of Compound A, Form I, and the grey line represents the diffractogram of Compound A, Form II.

In aspects of this embodiment, Compound A, Form I is characterized by an X-ray powder diffraction pattern substantially as shown in FIG. 1. In aspects of this embodiment, Compound A, Form I is characterized by an X-ray powder diffraction pattern substantially as shown in FIG. 2. In aspects of this embodiment, Compound A, Form II is characterized by an X-ray powder diffraction pattern substantially as shown in the black (darker) line in FIG. 12. In aspects of this embodiment, Compound A, Form II is characterized by an X-ray powder diffraction pattern substantially as shown in the black (darker) line in FIG. 13.

In aspects of this embodiment, Compound A, Form I is characterized by single crystal X-ray diffraction substantially as described by one or more of the characteristics recited in Table 2.

Figure 3:
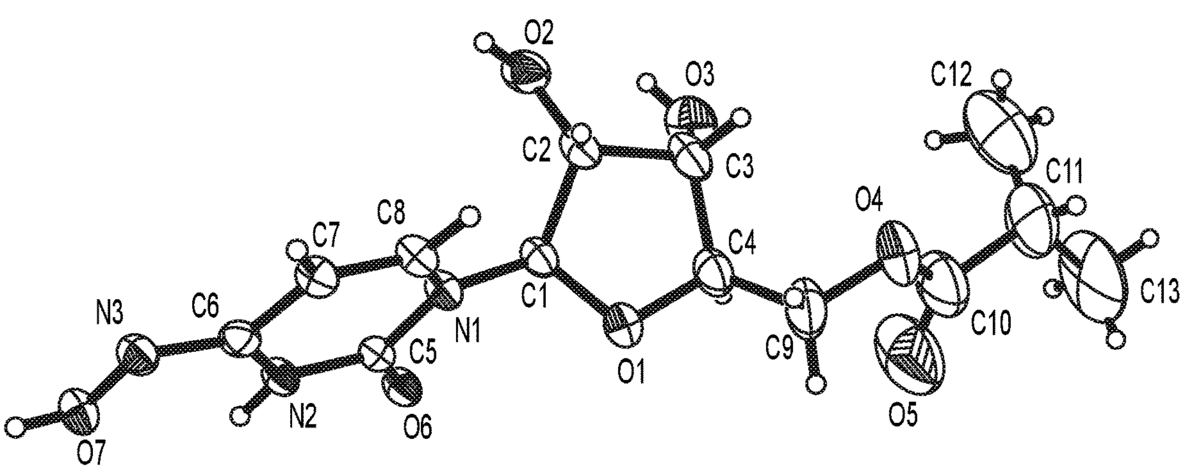
FIG. 3 depicts an ORTEP representation of Compound A, Form I.

In aspects of this embodiment, Compound A, Form I is characterized by an ORTEP representation substantially as shown in FIG. 3.

Figure 4:
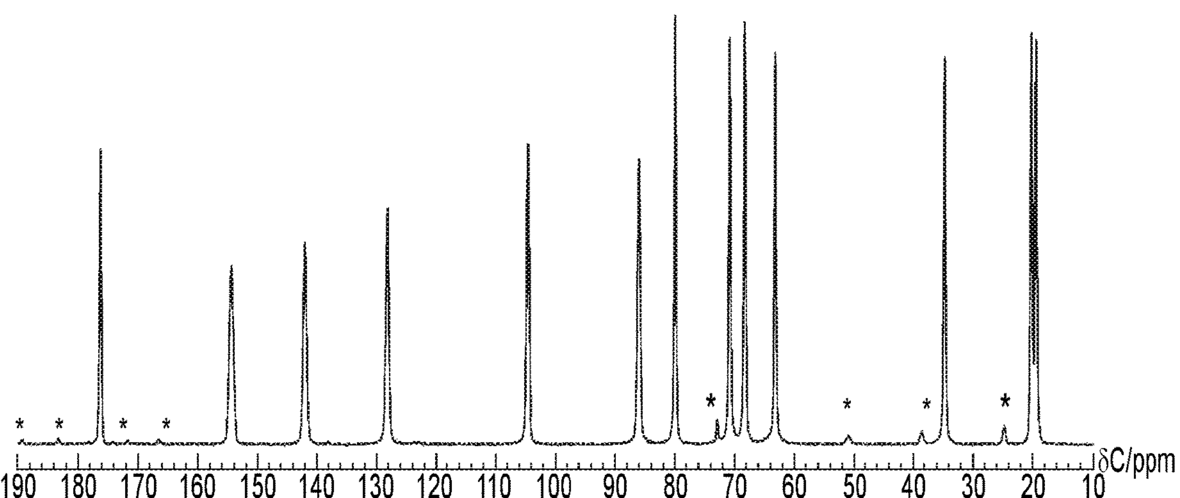
FIG. 4 depicts a carbon-13 cross-polarization magic-angle spinning (CPMAS) spectrum for Compound A, Form I.
Figure 5:
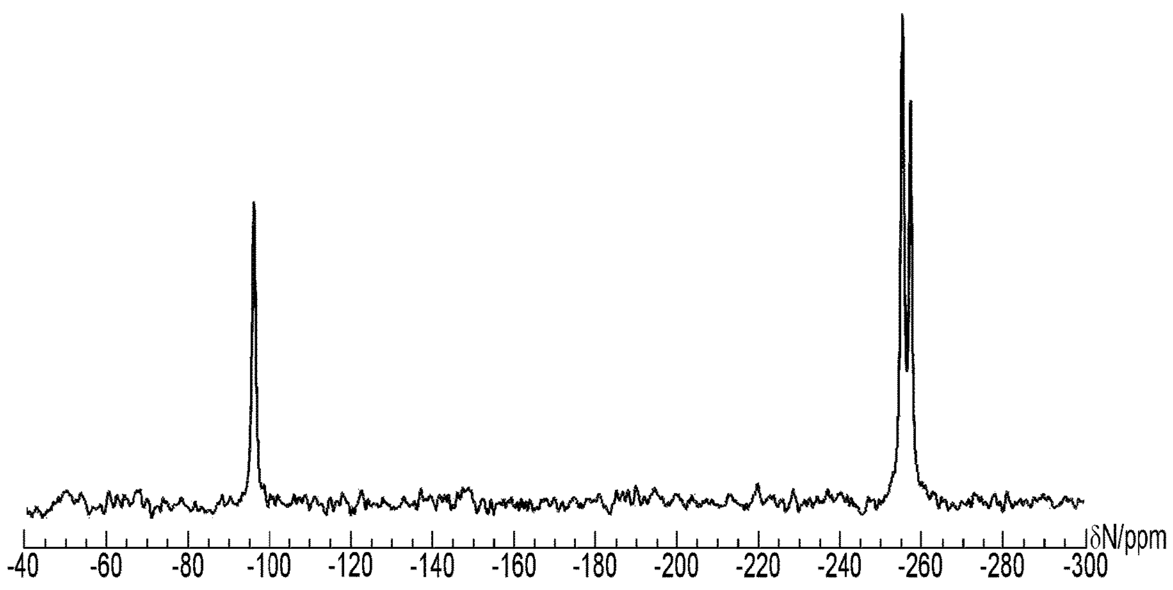
FIG. 5 depicts a nitrogen-15 CPMAS spectrum for Compound A, Form I.

In aspects of this embodiment, Compound A, Form I is characterized by a $^{13}C$ CPMAS spectrum substantially as shown in FIG. 4. In aspects of this embodiment, Compound A, Form I is characterized by a $^{15}N$ CPMAS spectrum substantially as shown in FIG. 5.

A second embodiment of the forms described herein is crystalline Form II of uridine 4-oxime 5'-(2-methylpropanoate) (Compound A, Form II), which is further described below.

In aspects of this embodiment, Compound A, Form II is crystallized from a solvent system comprising a solvent chosen from acetone, heptane, and mixtures thereof. In aspects of this embodiment, Compound A, Form II is crystallized from a solvent system comprising a solvent selected from the group consisting of acetone, heptane, and mixtures thereof. In specific aspects, heptane may be n-heptane; in other instances, heptane may be a mixture of heptanes. In a first instance, Compound A, Form II is crystallized from a solvent system, selected from the group consisting of acetone and heptane. In a second instance, Compound A, Form II may be crystallized from a solvent system that is a mixture of acetone and heptane.

Additional aspects of this second embodiment of the present disclosure provides a particular drug substance that comprises at least one of the forms described herein. The presence of a particular crystalline form in a drug substance can be detected by physical methods known to those of ordinary skill in art, such as X-ray powder diffraction (XRPD), single crystal X-ray diffraction, carbon-13 cross-polarization magic-angle spinning (CPMAS) nuclear magnetic resonance (NMR) spectroscopy, and nitrogen-15 CPMAS NMR spectroscopy.

In aspects of the second embodiment, Compound A, Form II is characterized by an X-ray powder diffraction pattern containing at least four ° 2θ values measured using CuKα radiation: about 17.7° 2θ, 18.2° 2θ, 18.9° 2θ, 21.0° 2θ, and 22.0° 2θ. In particular aspects, Compound A, Form II can also be characterized by an X-ray powder diffraction pattern containing at least four of ° 2θ values measured using CuKα radiation chosen from: 3.33° 2θ, about 6.61° 2θ, about 9.92° 2θ, about 13.23° 2θ, about 16.51° 2θ, about 17.82° 2θ, about 19.03° 2θ, about 22.10° 2θ, and about 23.85° 2θ. In particular aspects, Compound A, Form II is characterized by an X-ray powder diffraction pattern containing ° 2θ values measured using CuKα radiation at about 3.33° 2θ, about 17.82° 2θ, about 19.03° 2θ, and about 22.10° 20. In still more particular aspects, Compound A, Form II is characterized by an X-ray powder diffraction pattern containing at least four ° 2θ values measured using CuKα radiation chosen from: about 3.33° 2θ, about 6.61° 2θ, about 13.23° 2θ, about 17.82° 2θ, about 19.03° 2θ, about 22.10° 2θ, and about 23.85° 2θ. In further aspects, Compound A, Form II is characterized by an X-ray powder diffraction pattern containing at least five ° 2θ values measured using CuKα radiation chosen from: about 3.33° 2θ, about 6.61° 2θ, about 9.92° 2θ, about 13.23° 2θ, about 16.51° 2θ, about 17.82° 2θ, about 19.03° 2θ, about 22.10° 2θ, and about 23.85° 2θ.

In further aspects of the second embodiment, Compound A, Form II is characterized by an X-ray powder diffraction pattern containing at least four ° 2θ values measured using CuKα radiation chosen from: 3.33° 2θ±0.3° 2θ, 6.61° 2θ±0.3° 2θ, 9.92° 2θ±0.3° 2θ, 13.23° 2θ±0.3° 2θ, 16.51° 2θ±0.3° 2θ, 17.82° 2θ±0.3° 2θ, 19.03° 2θ±0.3° 2θ, 22.10° 2θ±0.3° 2θ, and 23.85° 2θ±0.3° 2θ. In particular aspects, Compound A, Form II is characterized by an X-ray powder diffraction pattern containing ° 2θ values measured using CuKα radiation at 3.33° 2θ±0.3° 2θ, 17.82° 2θ±0.3° 2θ, 19.03° 2θ±0.3° 2θ, and 22.10° 2θ+0.3° 2θ. In still more particular aspects, Compound A, Form II is characterized by an X-ray powder diffraction pattern containing at least four ° 2θ values measured using CuKα radiation chosen from: 3.33° 2θ±0.3° 2θ, 6.61° 2θ±0.3° 2θ, 13.23° 2θ±0.3° 2θ, 17.82° 2θ0.3° 2θ, 19.03° 2θ±0.3° 2θ, 22.10° 2θ±0.3° 2θ, and 23.85° 2θ±0.3° 2θ. In further aspects, Compound A, Form II is characterized by an X-ray powder diffraction pattern containing at least five ° 2θ values measured using CuKα radiation chosen from: 3.33° 2θ±0.3° 2θ, 6.61°2θ±0.3° 2θ, 9.92° 2θ±0.3° 2θ, 13.23° 2θ±0.3° 2θ, 16.51° 2θ±0.3° 2θ, 17.82° 2θ±0.3° 2θ, 19.03° 2θ±0.3° 2θ, 22.10° 2θ±0.3° 2θ, and 23.85° 2θ±0.3° 2θ.

In further aspects of the second embodiment, Compound A, Form II is characterized by an X-ray powder diffraction pattern containing at least four ° 2θ values measured using CuKα radiation chosen from: 3.33° 2θ±0.2° 2θ, 6.61° 2θ±0.2° 2θ, 9.92° 2θ±0.2° 2θ, 13.23° 2θ±0.2° 2θ, 16.51° 2θ±0.2° 2θ, 17.82° 2θ±0.2° 2θ, 19.03° 2θ±0.2° 2θ, 22.10° 2θ±0.2° 2θ, and 23.85° 2θ±0.2° 2θ. In particular aspects, Compound A, Form II is characterized by an X-ray powder diffraction pattern containing ° 2θ values measured using CuKα radiation at 3.33° 2θ±0.2° 2θ, 17.82° 2θ±0.2° 2θ, 19.03° 2θ±0.2° 2θ, and 22.10° 2θ±0.2° 2θ. In still more particular aspects, Compound A, Form II is characterized by an X-ray powder diffraction pattern containing at least four ° 2θ values measured using CuKα radiation chosen from: 3.33° 2θ±0.2° 2θ, 6.61° 2θ±0.2° 2θ, 13.23° 2θ±0.2° 2θ, 17.82° 2θ0.2° 2θ, 19.03° 2θ±0.2° 2θ, 22.10° 2θ±0.2° 2θ, and 23.85° 2θ±0.2° 2θ. In further aspects, Compound A, Form II is characterized by an X-ray powder diffraction pattern containing at least five ° 2θ values measured using CuKα radiation chosen from: 3.33° 2θ±0.2° 2θ, 6.61° 2θ±0.2° 2θ, 9.92° 2θ±0.2° 2θ, 13.23° 2θ±0.2° 2θ, 16.51° 2θ±0.2° 2θ, 17.82° 2θ±0.2° 2θ, 19.03° 2θ±0.2° 2θ, 22.10° 2θ±0.2° 2θ, and 23.85° 2θ±0.2° 2θ.

A further aspect of this embodiment is provided a composition comprising Compound A wherein Compound A is present at about 100% Compound A, Form II.

Further aspects of this embodiment include compositions comprising Compound A, wherein Compound A is present as 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, 50%, 49%, 48%, 47%, 46%, 45%, 44%, 43%, 42%, 4100, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 1%, 4%, %13%, %12%, 11%, 10%, 9%, 8%, 7%, 6%, 5%, 4%, 3%, 2%, or 1% Compound A, Form II. In a subaspect of this aspect of the disclosure, the balance of Compound A is present as Compound A, Form I.

In aspects of this embodiment, Compound A, Form II exists in from about 10% to about 100% of Compound A, Form II, such as from about 25% to about 98%, from about 50% to about 96%, from about 75% to about 95%, from about 90% to about 94%, or about 92%. In certain subaspects of this aspect, the balance of Compound A is present as Compound A, Form I.

Still another aspect of this embodiment is Compound A, Form II of 100%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 5100, 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5% 4%, 3%, 2%, or 1% purity.

Figure 6:
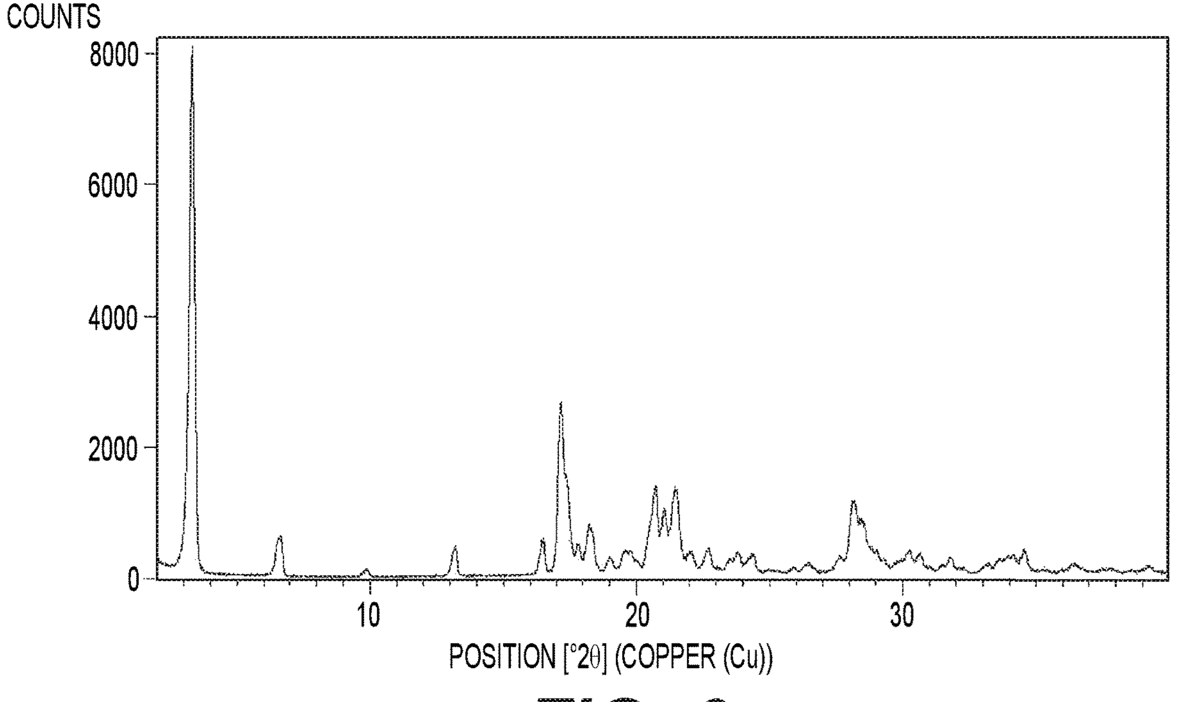
FIG. 6 depicts an X-ray powder diffraction pattern of Compound A, Form II, showing a range of 2°-40° 2θ.
Figure 7:
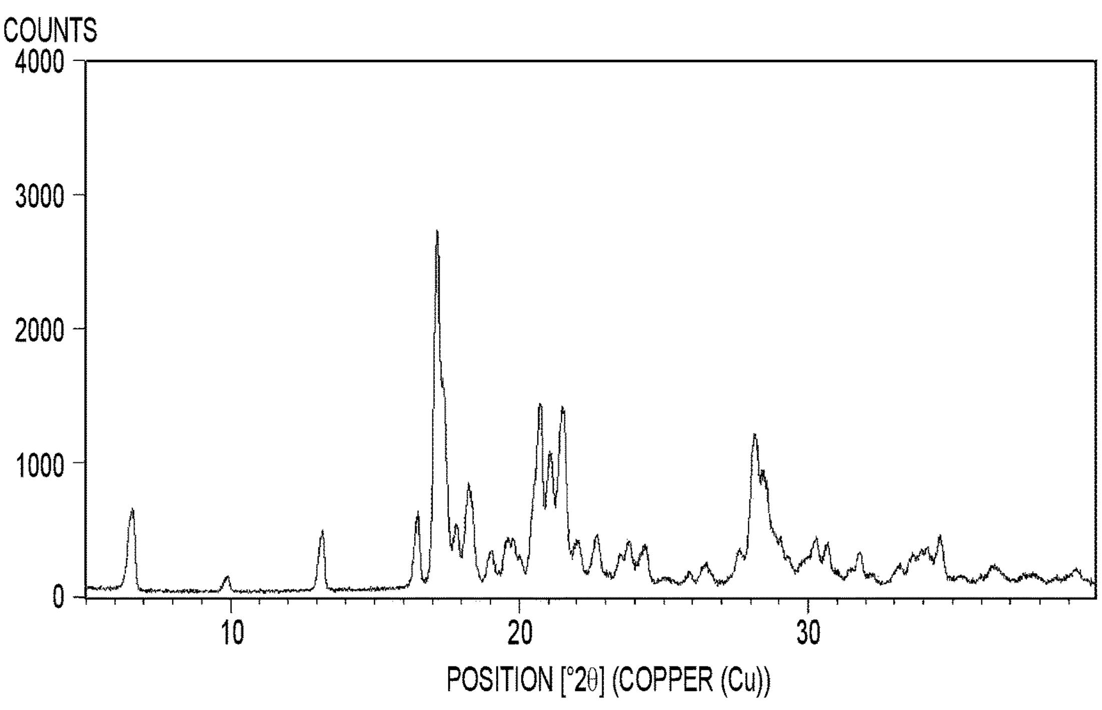
FIG. 7 depicts an X-ray powder diffraction pattern of Compound A, Form II, showing a range of 5°-40° 2θ.

In aspects of this embodiment, Compound A, Form II is characterized by an X-ray powder diffraction pattern substantially as shown in FIG. 6. In aspects of this embodiment, Compound A, Form II is characterized by an X-ray powder diffraction pattern substantially as shown in FIG. 7. In aspects of this embodiment, Compound A, Form II is characterized by an X-ray powder diffraction pattern substantially as shown in the grey line in FIG. 12. In aspects of this embodiment, Compound A, Form II is characterized by an X-ray powder diffraction pattern substantially as shown in the grey line in FIG. 13.

Figure 8:
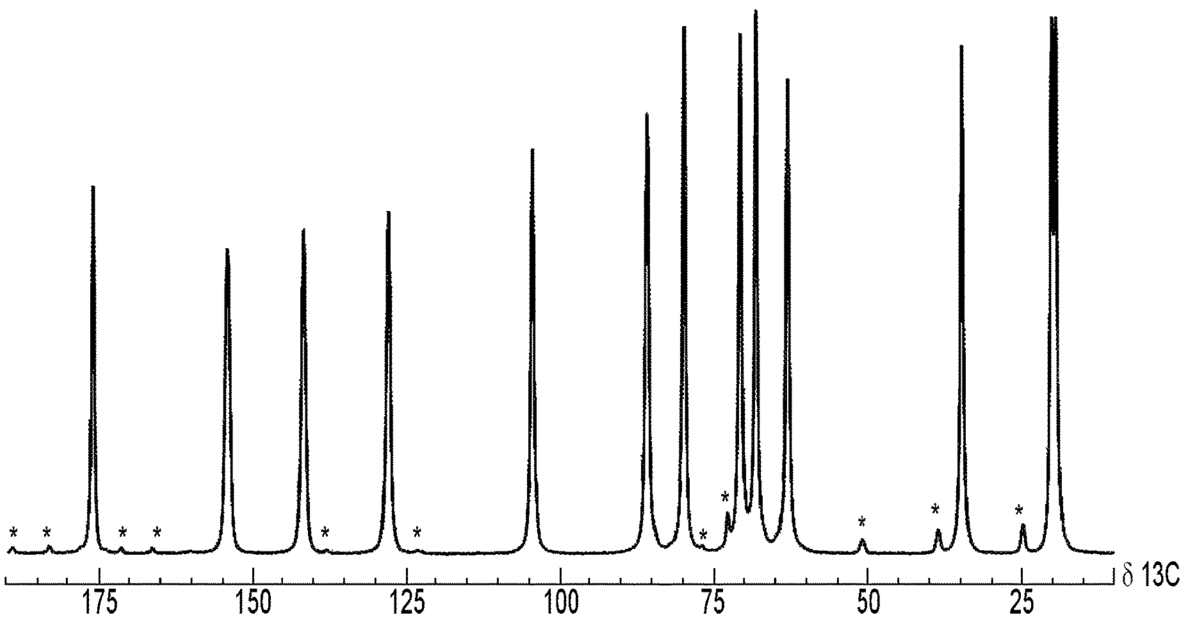
FIG. 8 depicts a carbon-13 cross-polarization magic-angle spinning (CPMAS) spectrum for Compound A, Form II.
Figure 9:
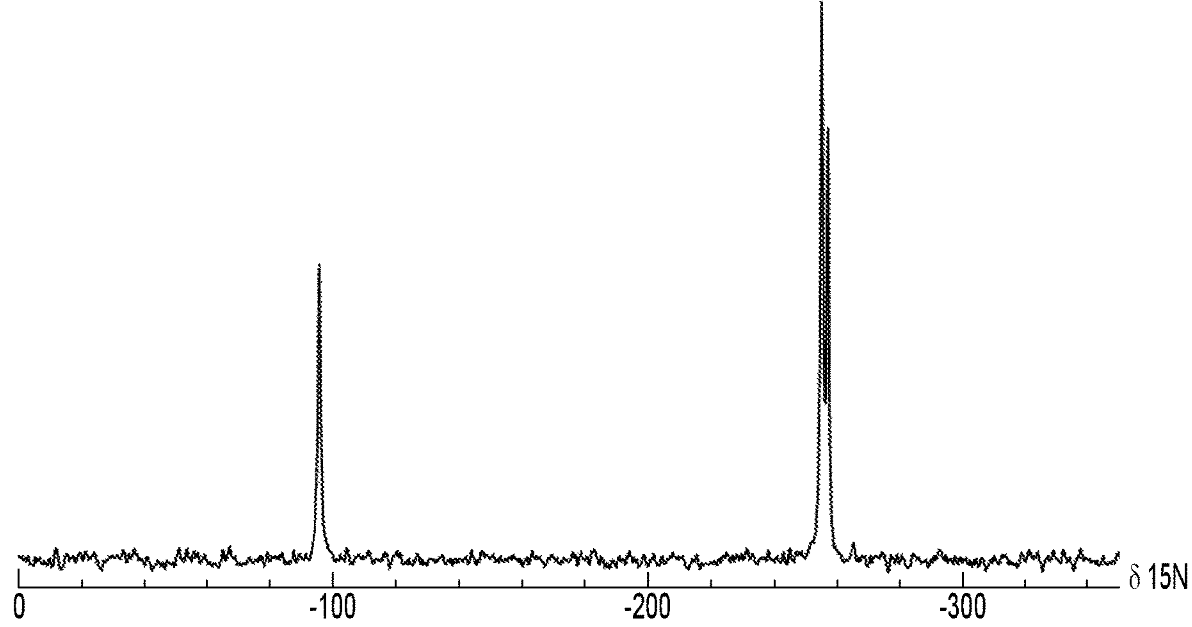
FIG. 9 depicts a nitrogen-15 CPMAS spectrum for Compound A, Form II.
Figure 10A:
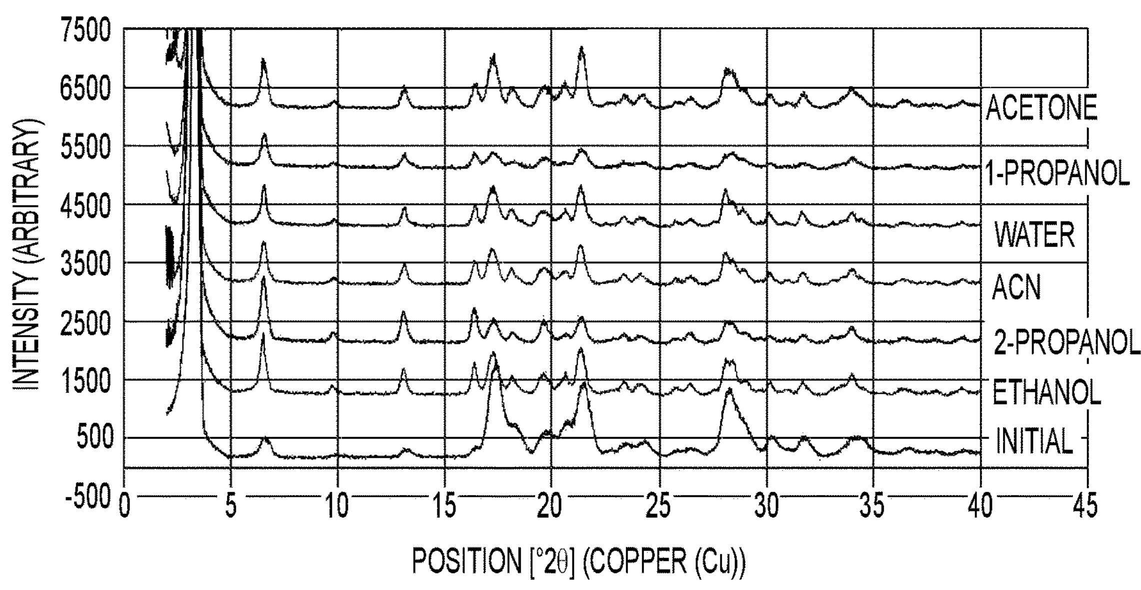
FIGS. 10A-10E depict X-ray powder diffraction patterns of products from crystallization experiments.
Figure 10B:
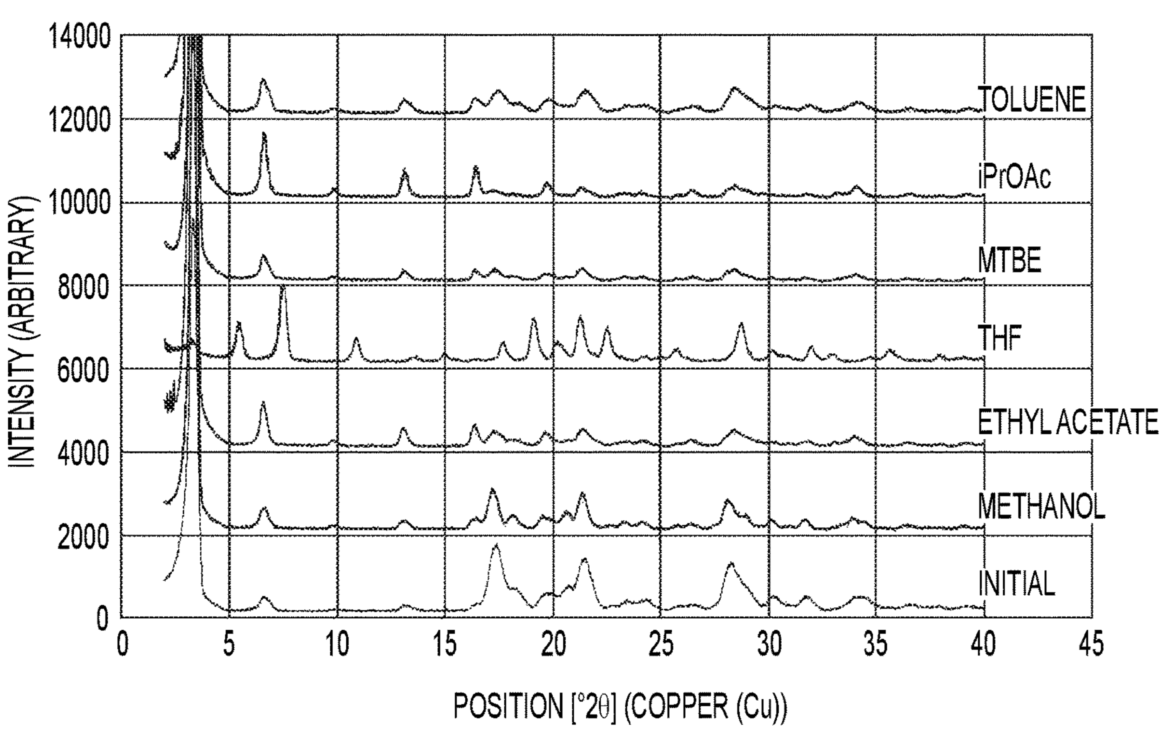
Figures 10C, 10D:
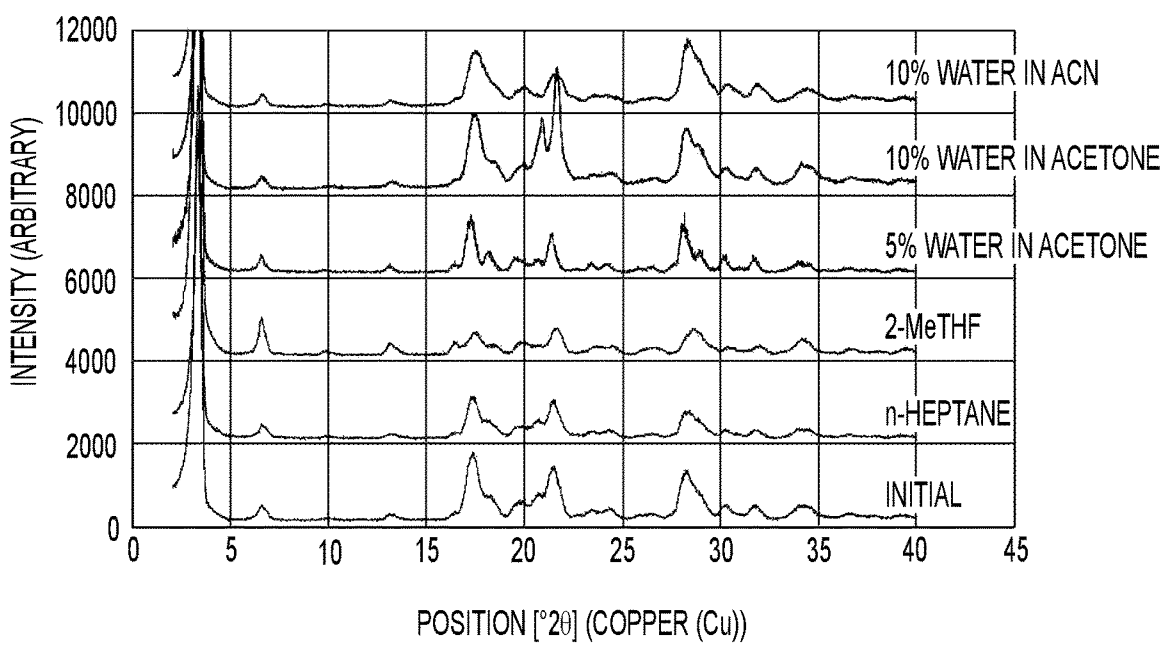
Figure 10E:
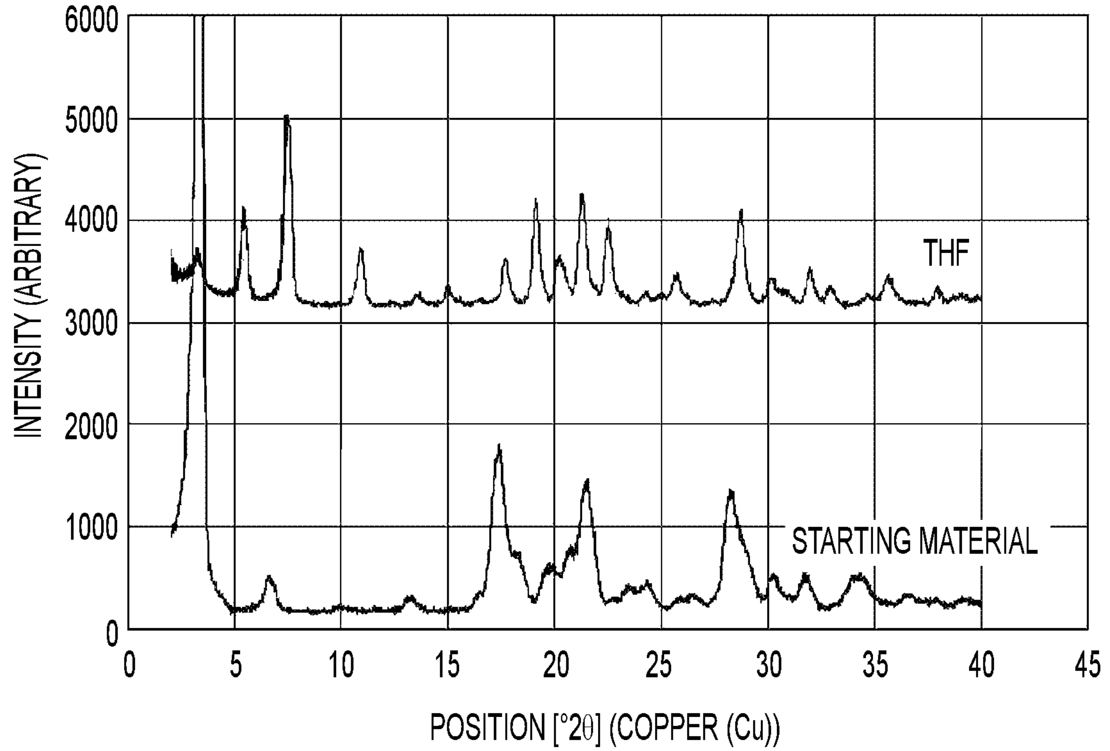
Figure 11A:
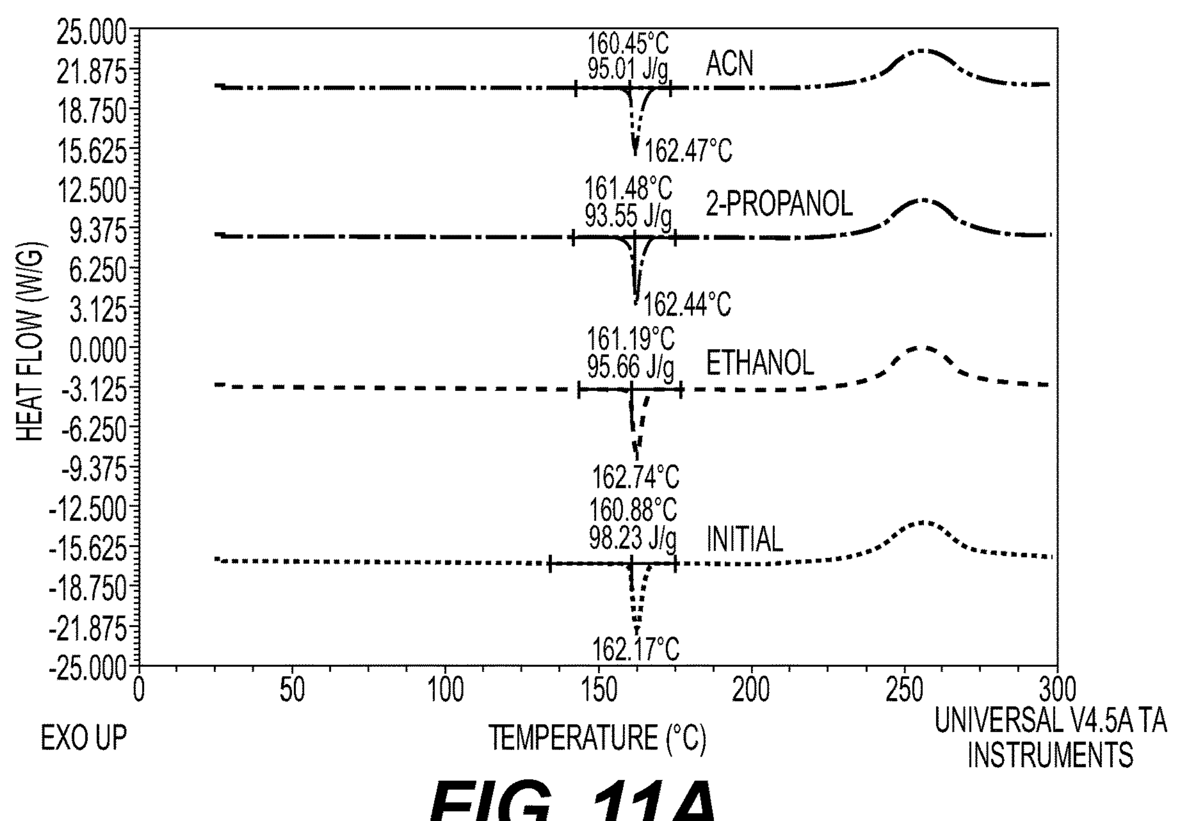
FIGS. 11A-11F depict DSC thermograms of products from crystallization experiments.
Figure 11B:
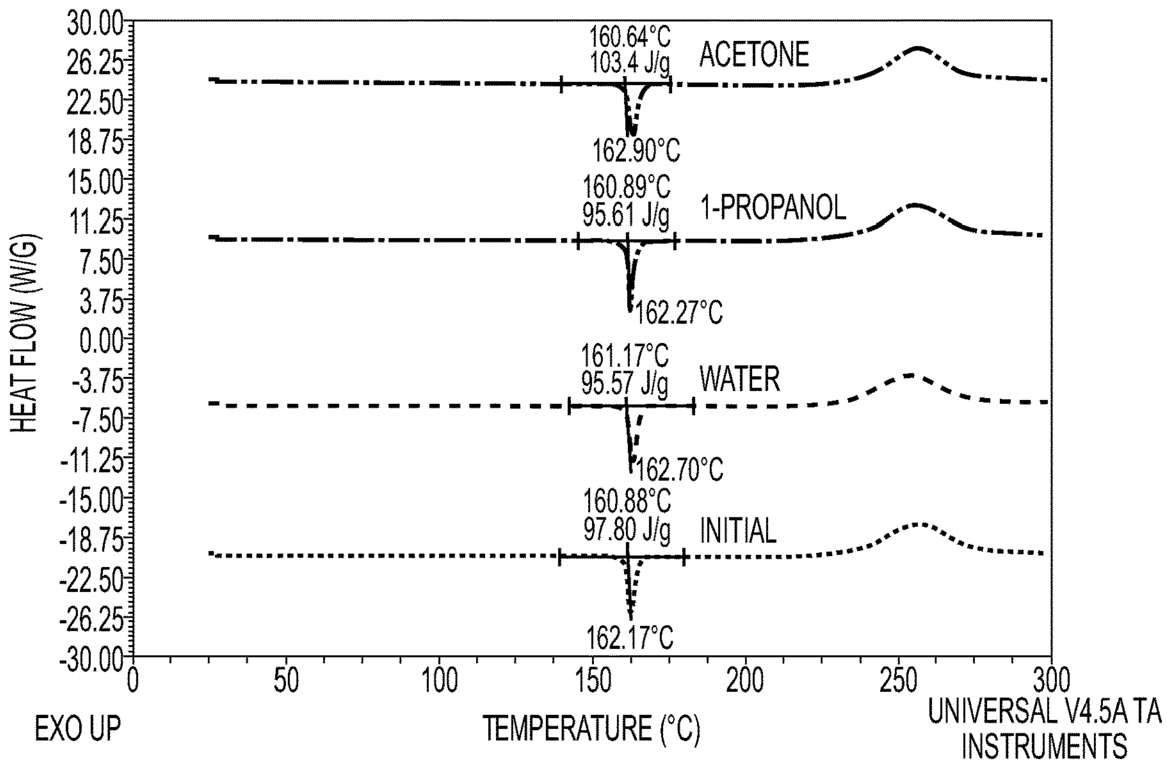
Figures 11C, 11D:
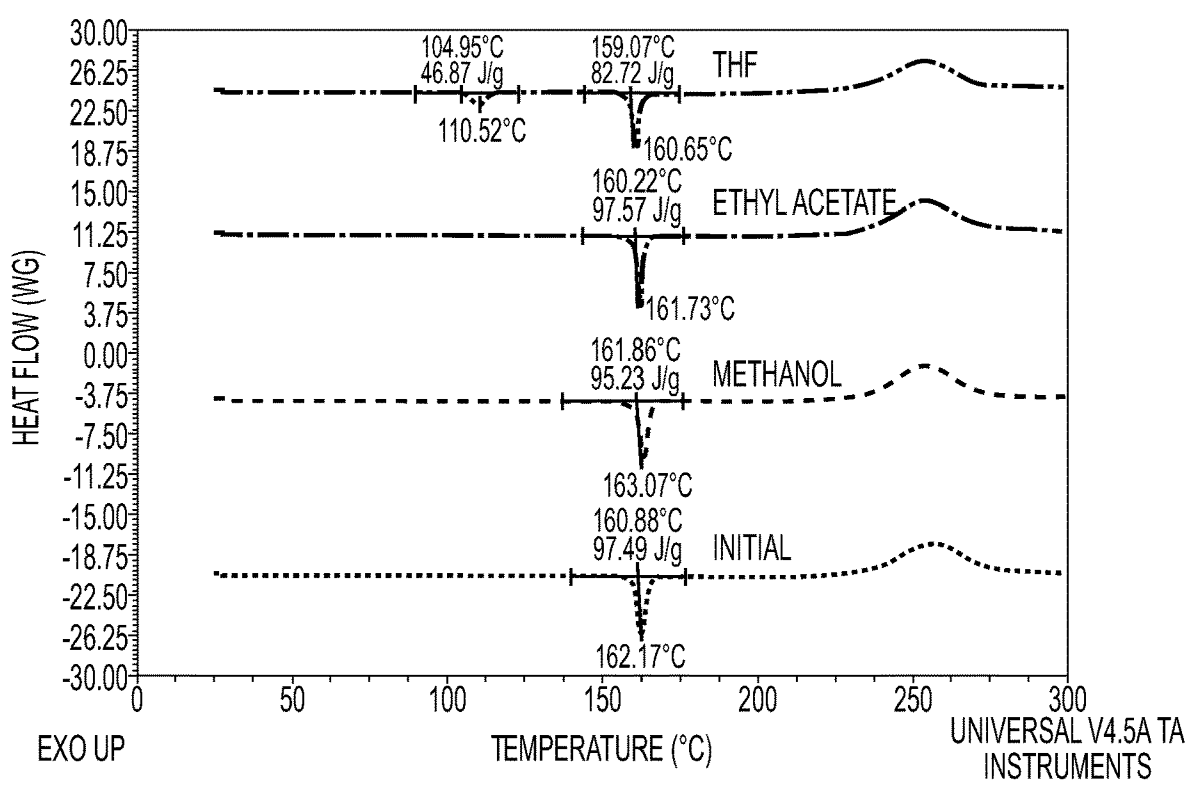
Figure 11E:
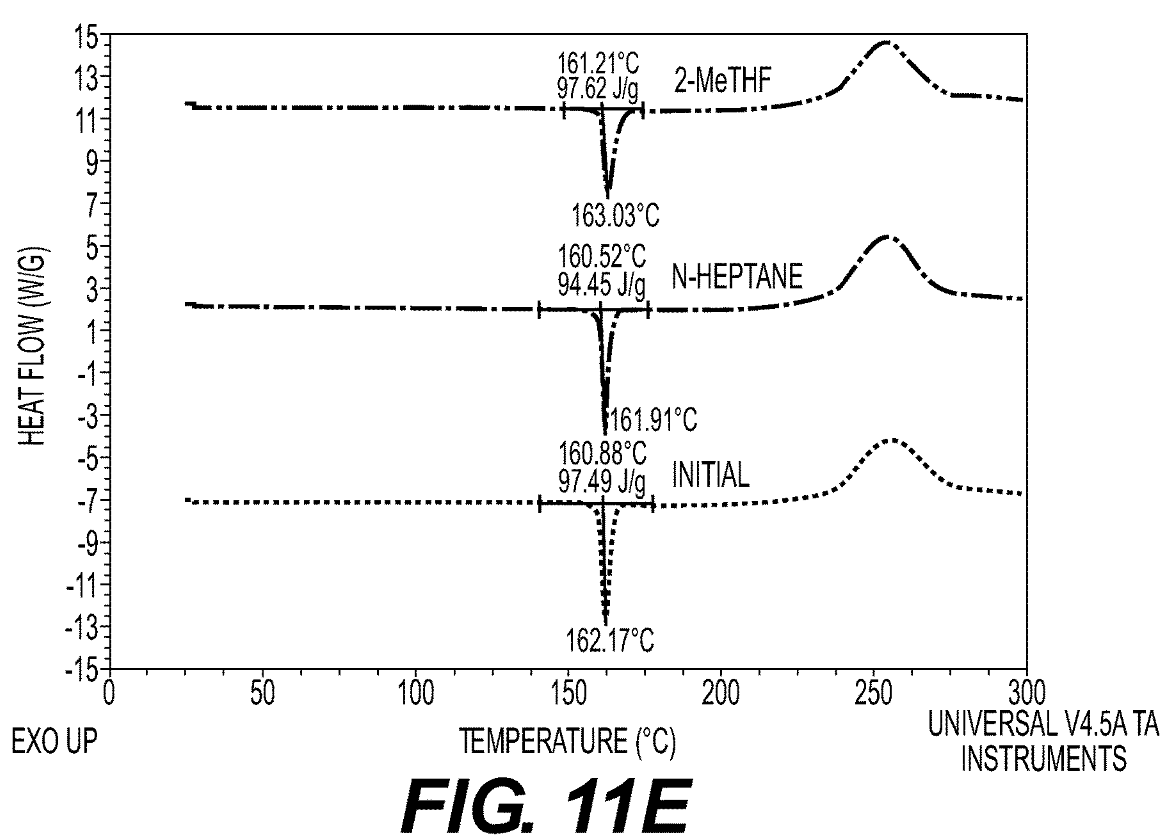
Figure 11F:
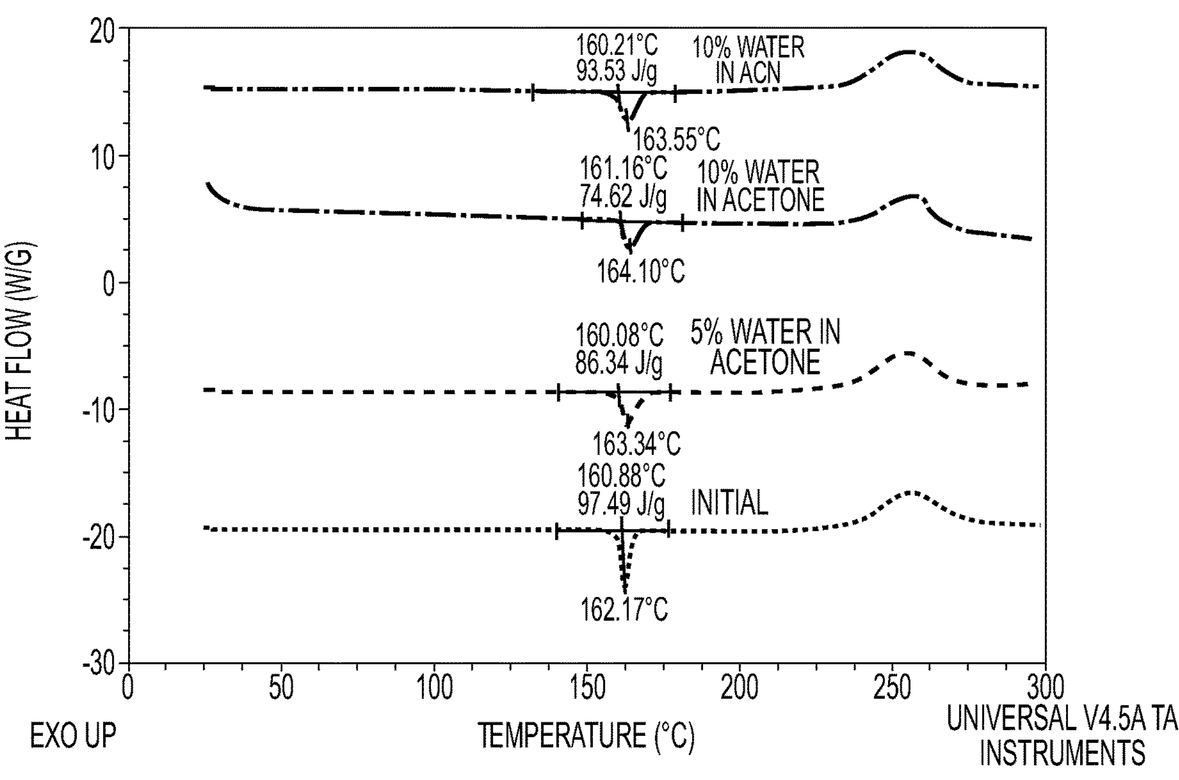

In aspects of this embodiment, Compound A, Form II is characterized by a $^{13}C$ CPMAS spectrum substantially as shown in FIG. 8. In aspects of this embodiment, Compound A, Form II is characterized by a $^{15}N$ CPMAS spectrum substantially as shown in FIG. 9.

Aspects of this third embodiment provide a THE solvate of uridine 4-oxime 5'-(2-methylpropanoate) in crystalline form. In additional aspects of this embodiment, Compound A, THF Solvate is crystallized from THF.

Additional aspects of this third embodiment of the present disclosure provides a particular drug substance that comprises at least one of the crystalline forms described herein. The presence of a particular crystalline form in the drug substance can be detected by physical methods known to one of ordinary skill in the art, such as X-ray powder diffraction (XRPD), single crystal X-ray diffraction, carbon-13 cross-polarization magic-angle spinning (CPMAS) nuclear magnetic resonance (NMR) spectroscopy, and nitrogen-15 CPMAS NMR spectroscopy.

In aspects of the third embodiment, Compound A, THF Solvate is characterized by an X-ray powder diffraction pattern according to FIG. 10. In other aspects of this embodiment, Compound A, THF Solvate is characterized by an X-ray powder diffraction pattern containing at least four ° 2θ values measured using CuKα radiation chosen from: about 5.40° 2θ, about 7.48° 2θ, about 10.92° 2θ, about 17.72° 2θ, about 19.14° 2θ, about 21.30° 2θ, about 22.56° 2θ, and about 28.76° 2θ. In particular aspects, Compound A, THF Solvate is characterized by an X-ray powder diffraction pattern containing ° 2θ values measured using CuKα radiation at about 5.40° 2θ, about 7.48° 2θ, about 10.92° 2θ, about 17.72° 2θ, about 19.14° 2θ, about 21.30° 2θ, about 22.56° 2θ, and about 28.76° 2θ.

Additional embodiments of the disclosure include pharmaceutical compositions comprising at least one of the crystalline forms described herein and a pharmaceutically acceptable carrier. The pharmaceutical compositions may be solid dosage forms for oral administration, such as tablets or capsules, liquid suspensions or formulations for oral administration, or sterile solutions for parenteral, intravenous, or intramuscular administration.

Further embodiments include the use of the crystalline forms described herein as an active ingredient in a medicament for inducing an antiviral response in a subject. Further embodiments include methods for inducing an antiviral response in a subject in need thereof comprising administering the crystalline forms described herein to the subject.

Further embodiments include the use of the pharmaceutical compositions described herein as a medicament for inducing an antiviral response in a subject. Further embodiments include method for inducing an antiviral response in a subject in need thereof comprising administering a pharmaceutical composition comprising crystalline forms described herein to the subject.

The crystalline forms of the present disclosure, such as Compound A, Form I, and Compound A, Form II, may exhibit properties such as stability, which may provide pharmaceutical advantages and may provide advantages in processability.

The dosage regimen is selected in accordance with a variety of factors including type, species, age, weight, sex, and medical condition of the patient; the severity of the condition to be treated; the route of administration; and the renal and hepatic function of the patient. An ordinarily skilled physician, veterinarian, or clinician can readily determine and prescribe the effective amount of the drug required to prevent, counter, or arrest the progress of the condition.

The forms of the present disclosure may be formulated and administered in solid dosage forms, such as tablets, pills, capsules, powders, or granules, which are intended for oral administration. Formulation of the compositions according to the disclosure can conveniently be by methods known from the art, for example, as described in Remington's Pharmaceutical Sciences, 18th ed., 1990, and Remington: The Science and Practice of Pharmacy, $22^{nd}$ ed., 2012. Furthermore, the forms of the present disclosure may be formulated and administered in sterile solutions for parenteral, intravenous, or intramuscular administration.

In the methods of the present disclosure, the forms described herein may be formulated as the active pharmaceutical ingredient, and may be administered in admixture with suitable pharmaceutical diluents, excipients, or carriers (collectively referred to herein as "carrier" materials) suitably selected with respect to the intended form of administration and consistent with conventional pharmaceutical practices, that is, oral tablets, oral capsules, oral suspensions, oral formulations, or sterile solutions for parenteral, intravenous, or intramuscular administration.

For instance, for oral administration in the form of a tablet or capsule, the form described herein can be combined with an oral, non-toxic, pharmaceutically acceptable, inert carrier (such as lactose, starch, sucrose, glucose, methyl cellulose, magnesium stearate, dicalcium phosphate, calcium sulfate, mannitol, sorbitol, and the like). For parenteral, intravenous, or intramuscular administration in the form of a sterile solution, the form described herein may be combined with suitable excipients and non-toxic, pharmaceutically acceptable, inert carrier into a formulation that may be provided as a prepared dosage form in a pre-filled injection apparatus, as a lyophilized formulation to be reconstituted for injection, or as a sterile liquid to be diluted for injection.

Methods for preparing 3-D-N(4)-hydroxycytidine (NHC), and derivatives thereof are disclosed in PCT International Patent Application No. PCT/US2015/066144, which published as PCT International Patent Application Publication No. WO2016/106050. Methods of preparing Compound A, and tautomers and derivatives thereof are disclosed in PCT International Patent Application No. PCT/US2018/064503, which published as PCT International Patent Application Publication No. WO2019/113462, and in U.S. patent application Ser. No. 16/755,779, and in U.S. Provisional Patent Application No. 63/127,484, which are incorporated herein by reference in their entirety.

Some aspects and embodiments disclosed herein include:

1. Crystalline Form I of {(2R,3S,4R,5R)-3,4-dihydroxy-5-[(4Z)-4-(hydroxyimino)-2-oxo-3,4-dihydropyrimidin-1(2H)-yl]oxolan-2-yl}methyl 2-methylpropanoate.
2. The crystalline form according to embodiment 1, wherein said crystalline form has a monoclinic crystal system.
3. The crystalline form according to any one of embodiments 1 and 2, wherein said crystalline form is prepared by crystallization from ethyl acetate and MTBE.
4. The crystalline form according to any one of embodiments 1 and 2, wherein said crystalline form is prepared by crystallization from acetone and n-heptane vapors.
5. The crystalline form according to any one of embodiments 1 and 2, wherein said crystalline form is prepared by crystallization from water.
6. The crystalline form according to any one of embodiments 1-5, characterized by an X-ray powder diffraction pattern containing ° 2θ values measured using CuKα radiation at about 3.34° 2θ, about 19.51° 2θ, about 19.97° 2θ, and about 21.47° 2θ.
7. The crystalline form according to any one of embodiments 1-5, characterized by an X-ray powder diffraction pattern containing at least four ° 2θ values measured using CuKα radiation chosen from: about 3.34° 2θ, about 6.53° 2θ, about 13.11° 2θ, about 18.13° 2θ, about 19.51° 2θ, about 19.97° 2θ, and about 21.47° 2θ.
8. The crystalline form according to any one of embodiments 1-5, characterized by having an X-ray powder diffraction containing at least five ° 2θ values measured using CuKα radiation chosen from: about 3.34° 2θ, about 6.53° 2θ, about 13.11° 2θ, about 17.06° 2θ, about 17.33° 2θ, about 18.13° 2θ, about 19.51° 2θ, about 19.97° 2θ, and about 21.47° 2θ.
9. Crystalline Form II of {(2R,3S,4R,5R)-3,4-dihydroxy-5-[(4Z)-4-(hydroxyimino)-2-oxo-3,4-dihydropyrimidin-1(2H)-yl]oxolan-2-yl}methyl 2-methylpropanoate.
10. The crystalline form according to embodiment 9, wherein said crystalline form is prepared by crystallization from acetone and n-heptane.
11. The crystalline form according to any one of embodiments 9 and 10, characterized by an X-ray powder diffraction pattern containing at least four ° 2θ values measured using CuKα radiation chosen from: about 3.33° 2θ, about 6.61° 2θ, about 9.92° 2θ, about 13.23° 2θ, about 16.51° 2θ, about 17.82° 2θ, about 19.03° 2θ, about 22.10° 2θ, and about 23.85° 2θ.
12. The crystalline form according to any one of embodiments 9 and 10, characterized by an X-ray powder diffraction pattern containing ° 2θ values measured using CuKα radiation at: about 3.33° 2θ, about 17.82° 2θ, about 19.03° 2θ, and about 22.10° 2θ.
13. The crystalline form according to any one of embodiments 9 and 10, characterized by an X-ray powder diffraction pattern containing at least 4° 2θ values measured using CuKα radiation chosen from: about 17.7° 2θ, about 18.2° 2θ, about 18.9° 2θ, about 21.0° 2θ, and about 22.0° 2θ.

14. The crystalline form according to any one of embodiments 9 and 10, characterized by an X-ray powder diffraction pattern containing at least 4° 2θ values measured using CuKα radiation chosen from: about 3.33° 2θ, about 6.61° 2θ, about 9.92° 2θ, about 13.23° 2θ, about 16.51° 2θ, about 17.82° 2θ, about 19.03° 2θ, about 22.10° 2θ, and about 23.85° 2θ.

15. A pharmaceutical composition comprising at least one crystalline form according to any one of embodiments 1-14 and a pharmaceutically acceptable carrier.

16. The pharmaceutical composition according to embodiment 15, wherein the pharmaceutical composition is a solid dosage form for oral administration.

17. Use of the crystalline form according to any one of embodiments 1-14 as an active ingredient in a medicament for inducing an antiviral response in a subject.

18. Use of the pharmaceutical composition according to any one of embodiments 15-16 as a medicament for inducing an antiviral response in a subject.

19. Use of the crystalline form according to any one of embodiments 1-14 as an active ingredient in a medicament for inducing an antiviral response to SARS-CoV-2 infection in a subject.

20. Use of the pharmaceutical composition according to any one of embodiments 15-16 as a medicament for inducing an antiviral response to SARS-CoV-2 infection in a subject.

Abbreviations

Å Angstrom, 0.1 nanometer
C2 Crystallographic space group
D Density ($g/cm^3$)
DMAP 4-dimethylaminopyridine
equiv Equivalents
F Structure Factor
MTBE Methyl tert-butyl ether
R R-factor
S Goodness-of-fit on $F^2$
THF Tetrahydrofuran
TMS Tetramethylsilane
V Volume
$wR^2$ R-factor determined from $F^2$
Z Formula units in unit cell
Z' Number of molecules in the asymmetric unit
σ Standard deviation

EXAMPLES

Example 1: Synthesis of Uridine 4-Oxime 5'-(2-Methylpropanoate) (Compound A, Form I)

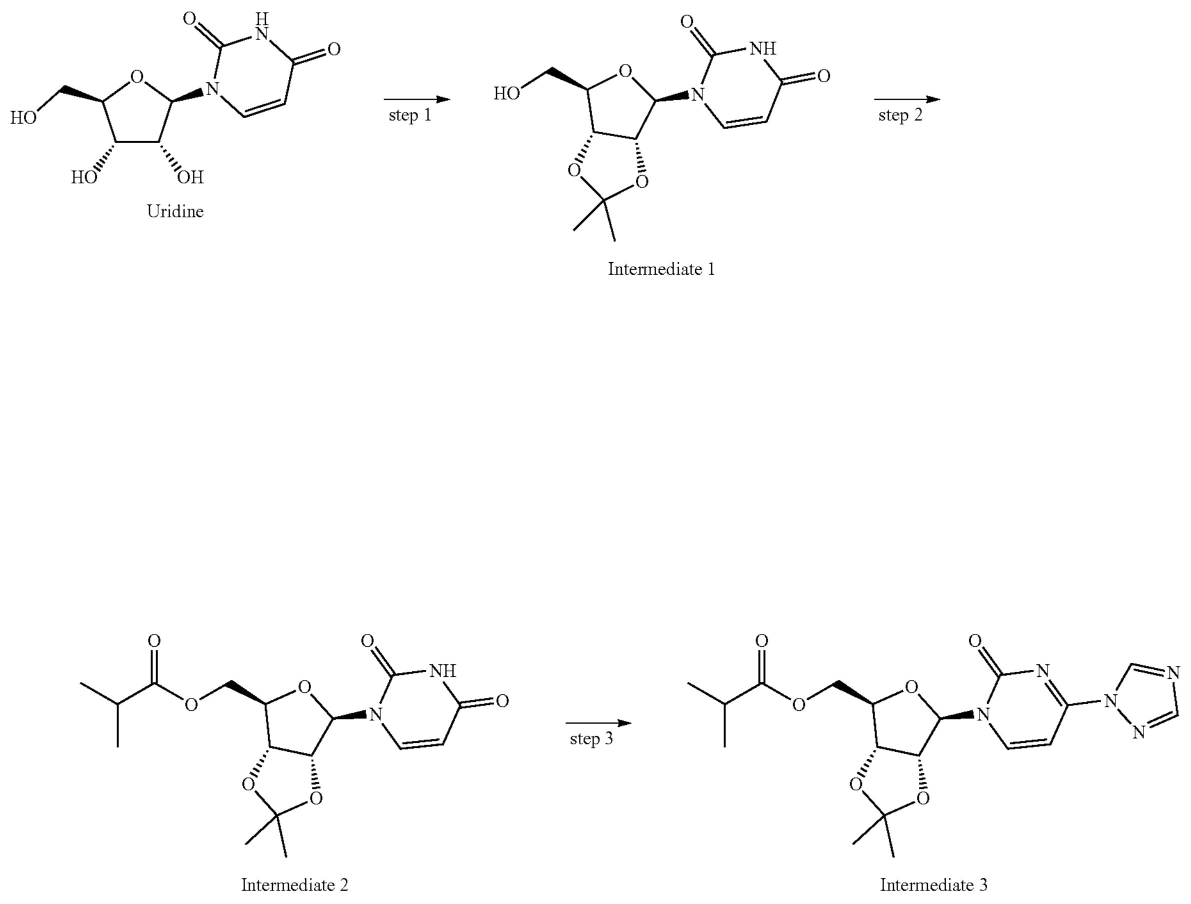

Uridine

Intermediate 1

Intermediate 2

Intermediate 3

-continued

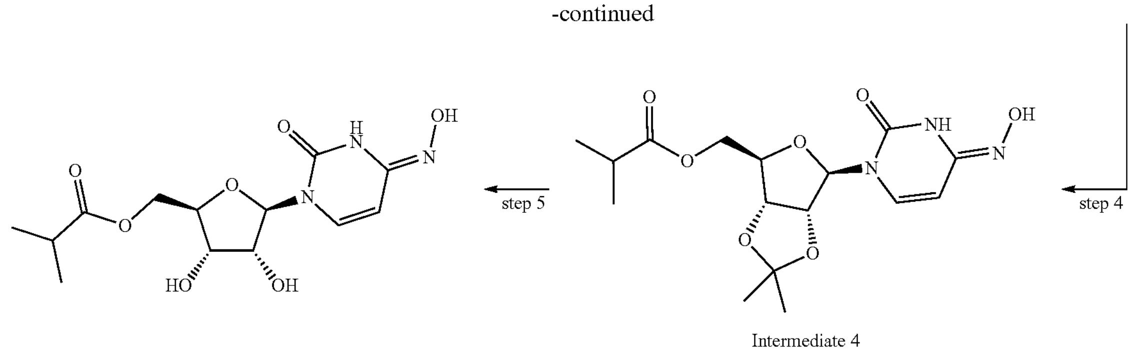

A 100 L cylindrical vessel was charged with uridine (11.66 kg), acetone (70 L), 2,2-dimethoxypropane (1.05 equiv), and sulfuric acid (0.01 equiv). The reaction mixture was heated at 50° C.-57° C. until the reaction was deemed complete. Triethylamine (0.04 equiv) was added, followed by seed, and the slurry was cooled to 0° C.-5° C. The crystalline solid was collected and washed with MTBE to afford Intermediate 1.

Intermediate 1 was charged into a 100 L cylindrical vessel, followed by ethyl acetate (40 L), triethylamine (1.44 equiv), and DMAP (0.02 equiv). The mixture was cooled, and isobutyric acid was added slowly. The reaction mixture was aged at 20° C.-25° C. until full conversion was observed. The organic solution was washed twice with water, then azeotropically dried to afford a 29.4 wt % solution of Intermediate 2 in ethyl acetate.

In a 100 L cylindrical vessel was mixed 1,2,4-triazole (4.94 equiv), acetonitrile (36 L), triethylamine (6.88 equiv), and $POCl_3$ (1.28 equiv). A portion of the solution of Intermediate 2 (22.9 mol) was added to the vessel, and the resulting mixture was aged at ambient temperature overnight. Ethyl acetate was added, and the organic solution was washed twice with water. The solvent was exchanged for dry isopropanol by distillation, and n-heptane was added to crystallize Intermediate 3, which was collected by filtration and washed with MTBE.

A mixture of Intermediate 3 and acetonitrile (15 L) was cooled in a 100 L cylindrical vessel and reacted with aqueous hydroxylamine (1.3 equiv) until the reaction was deemed complete. Water was added, and the crystalline product was isolated by filtration and washed with water to afford Intermediate 4.

Intermediate 4 (5.96 kg) was added to a 100 L cylindrical vessel, along with acetonitrile (60 L) and aqueous HCl (1.27 equiv). The reaction was aged at 31° C.-33° C. until the reaction was deemed complete. The acid was quenched with aqueous sodium carbonate and the acetonitrile was replaced with ethyl acetate through distillation. The organic phase was washed with 22 wt % aqueous sodium sulfate and water. The resulting ethyl acetate solution was azeotropically dried to crystallize the product. MTBE was added, and the product was collected by filtration and washed with a mixture of ethyl acetate and MTBE to afford uridine 4-oxime 5'-(2-methylpropanoate) (Compound A, Form I).

Example 2: Recrystallization of Uridine 4-Oxime 5'-(2-Methylpropanoate) (Compound A, Form I)

Compound A, Form I, was recrystallized by dissolving Compound A, Form I, from the above synthesis in acetone, heating to 50° C., allowing the solution to cool to room temperature, and exposing the solution to n-heptane vapors by vapor diffusion.

Example 3: X-Ray Powder Diffraction Characterization of Compound A, Form I

X-ray powder diffraction (XRPD) studies are widely used to characterize molecular structures, crystallinity, and polymorphism. The X-ray powder diffraction patterns for Compound A, Form I, were generated on a Panalytical Empyrean X-ray Diffraction System. A Cu K-Alpha radiation source was used. The experiments were analyzed at ambient conditions.

Analysis was performed on Compound A, Form I, as provided in Example 2. FIG. 1 shows peaks for Compound A, Form I, in the range of 2°-40° 2θ. FIG. 2 shows peaks for Compound A, Form I, in the range of 5°-40° 2θ. The X-ray powder diffraction pattern was generated to characterize Compound A, Form I, as shown in FIG. 1, which exhibited reflections corresponding to d-spacings (±0.3° 2 theta) as shown in Table 1.

TABLE 1

| Position (° 2θ)(±0.3° 2θ) | d-spacing (Å) | Relative Intensity (%) |
|---|---|---|
| 3.34 | 26.45 | 100.0 |
| 6.53 | 13.55 | 7.2 |
| 9.81 | 9.02 | 0.8 |
| 13.11 | 6.75 | 2.8 |
| 16.41 | 5.40 | 3.3 |
| 17.06 | 5.20 | 19.7 |
| 17.33 | 5.12 | 19.5 |
| 18.13 | 4.89 | 10.0 |
| 18.49 | 4.80 | 2.0 |
| 19.51 | 4.55 | 6.0 |
| 19.97 | 4.45 | 4.0 |
| 20.40 | 4.35 | 6.1 |
| 20.68 | 4.30 | 11.8 |
| 21.47 | 4.14 | 20.3 |
| 22.63 | 3.93 | 1.4 |
| 23.43 | 3.80 | 3.0 |
| 24.05 | 3.70 | 1.9 |
| 24.36 | 3.65 | 2.2 |
| 25.84 | 3.45 | 1.2 |
| 26.55 | 3.36 | 1.4 |
| 27.57 | 3.24 | 1.8 |
| 28.17 | 3.17 | 14.9 |
| 28.52 | 3.13 | 5.0 |
| 29.00 | 3.08 | 4.7 |
| 30.22 | 2.96 | 4.1 |
| 31.03 | 2.88 | 0.9 |
| 31.76 | 2.82 | 3.3 |
| 34.08 | 2.63 | 2.4 |

TABLE 1-continued

| Position (° 2θ)(±0.3° 2θ) | d-spacing (Å) | Relative Intensity (%) |
|---|---|---|
| 34.58 | 2.59 | 2.2 |
| 36.26 | 2.48 | 0.7 |
| 36.74 | 2.45 | 0.8 |
| 37.42 | 2.40 | 0.8 |
| 38.01 | 2.37 | 0.5 |
| 38.87 | 2.32 | 0.4 |

Example 4: Single Crystal Crystallographic Characterization of Compound A, Form I A single crystal was obtained by heating a water solution saturated in Compound A to 70° C. until dissolution completed, followed by slow cooling to room temperature. Single crystal structure determination was performed using a Bruker APEX II CCD diffractometer. Cell determinations and diffraction data (98.4 completeness to 0.84 Å resolution) were measured using monochromatized Cu Kα radiation. Full data acquisition for structure solution was performed at 293K. The crystal structure of Compound A, Form I, was solved by single crystal X-ray analysis. Crystallographic details are shown in Table 2. An ORTEP representation of Compound A, Form I, is shown in FIG. 3. Ellipsoids are shown at the 30% probability level.

TABLE 2

| | |
|---|---|
| Formula, Formula weight | $C_{13}H_{19}N_3O_7$, 329.31 |
| Crystal system, Space group | monoclinic, C2 |
| Cell lengths (Å) | a = 6.5022 (6), b = 8.7080 (6), c = 27.1375 (19) |
| Cell angles | α = 90, β = 92.169(7), γ = 90 |
| V(Å$^3$), Z, Z', D (calculated) | 1535.5(2), 4, 1, 1.425 |
| M (Cu Kα) (mm$^{-1}$) | 0.997 |
| F (000) | 696.0 |
| Crystal size (mm) | 0.1 × 0.05 × 0.005 |
| Temperature (K) | 293 |
| Radiation (Å) | Cu Kα (1.54178) |
| Instrument | Bruker APEX II |
| Resolution (Å$^{-3}$), max 2 theta (°) | 0.84, 133.19 |
| Reflections: (Total, Unique, 2σ observed) | 9016, 2628, 2117 |
| Refined parameters | 221 |
| R, wR$_2$, S | 0.0488, 0.1269, 1.016 |
| Max. shift/error | 0.00 |
| Max. residual density [e Å$^{-3}$] | 0.16 |

Example 5: Solid-State NMR Characterization of Compound A, Form I

A sample of Compound A, Form I, was characterized by the respective carbon-13 and nitrogen-15 solid-state NMR (ssNMR) spectra. ssNMR carbon-13 and nitrogen-15 spectra were recorded on a Bruker AV500 NMR spectrometer operating at 125.76 MHz and 50.68 MHz, respectively, using a Bruker 4 mm H/F/X BB double resonance CPMAS probe. The spectra were collected utilizing proton to carbon-13 and proton to nitrogen-15 cross-polarization (CP) with contact times of 3 ms and 7 ms, respectively. A 100 kHz-spin lock and an 83.3 kHz square contact pulse were used for CP on the proton channel. Linearly ramped contact pulse, starting at 50% and ending at 100% with respect to pulse power, with the respective power calibrated to produce maximum signal, were applied during cross-polarization on the carbon-13 and nitrogen-15 channels. Other experimental parameters used for data acquisition were a proton 90-degree pulse of 100 kHz, proton two pulse phase modulation (TPPM) decoupling during acquisition at 100 kHz, and a pulse delay of 3.5 s. 4600 and 16000 scans for signal averaging were collected for the carbon-13 and nitrogen-15 spectra, respectively. Carbon-13 and nitrogen-15 spectra were acquired utilizing a magic-angle spinning (MAS) rate of 13 kHz. A Lorentzian line broadening of 30 Hz was applied to the carbon-13 and nitrogen-15 spectra before Fourier Transformation. Chemical shifts are reported on the TMS scale by using the carbonyl carbon and the amine nitrogen in glycine as secondary references. The carbonyl carbon was set to 176.70 ppm and the amine nitrogen was set to −346.40 ppm to reference the carbon-13 and nitrogen-15 CPMAS spectra, respectively.

Carbon-13 peaks are observed at 19.41, 20.18, 34.70, 63.14, 68.22, 70.74, 79.86, 85.92, 104.65, 128.08, 141.91, 154.31, and 176.21 ppm (±0.03 ppm). Nitrogen-15 peaks are observed at −257.04, −255.06, and −95.43 ppm (±0.03 ppm). FIG. 4 and FIG. 5 show the carbon-13 and nitrogen-15 CPMAS spectra for Compound A, Form I, respectively. In the carbon-13 CPMAS spectrum, spinning sidebands are indicated by asterisks.

Example 6: Capsule Formulation

As a specific embodiment of an oral capsule pharmaceutical composition, a 200 mg potency capsule is composed of 200 mg of Compound A, Form I, 67.1 mg of microcrystalline cellulose, 8.6 mg of hydroxypropyl cellulose, 8.6 mg of croscarmellose sodium, and 1.4 mg of magnesium stearate. Compound A, Form I, microcrystalline cellulose, hydroxypropyl cellulose, and croscarmellose sodium are high-shear wet granulated, wet milled, dried, dry milled, and lubricated with magnesium stearate followed by encapsulation into hydroxypropyl methylcellulose capsules.

Example 7: Tablet Formulation

As a specific embodiment of an oral tablet pharmaceutical composition, a 200 mg potency tablet is composed of 200 mg of Compound A, Form I, 21.25 mg microcrystalline cellulose, 21.25 mg of lactose, 6.00 mg of croscarmellose sodium, and 1.50 mg of magnesium stearate. The Compound A, Form I, microcrystalline cellulose, lactose, and half of the croscarmellose sodium are blended first. The mixture is then lubricated by half of the magnesium stearate and dry granulated using a roller compactor. The remaining croscarmellose sodium is added to the mixture and blended. The remaining half of the magnesium stearate is then added to the mixture and lubricated. The mixture is then pressed into tablets.

Example 8: Recrystallization of Uridine 4-Oxime 5'-(2-Methylpropanoate) (Compound A, Form II)

A 1 L vessel was charged with Compound A, Form I (14.9 g, Example 1), and acetone (0.25 L). The reaction mixture was heated at 52° C. until the mixture was a solution. In a separate 3 L vessel was charged n-heptane (1.5 L), which was stirred vigorously and adjusted to 20° C. The dissolved solution was added in one shot to the n-heptane-containing vessel at 20° C., resulting in precipitation of Compound A, Form II. The slurry was stirred for 15 minutes. The product was collected by filtration and was washed with n-heptane. The batch was dried at 25° C. under vacuum to afford 13.2 g of uridine 4-oxime 5'-(2-methylpropanoate) (Compound A, Form II).

Example 9: X-Ray Powder Diffraction Characterization of Compound A, Form II

X-ray powder diffraction (XRPD) studies are widely used to characterize molecular structures, crystallinity, and polymorphism. The X-ray powder diffraction patterns for Compound A, Form II, were generated on a Panalytical Empyrean X-ray Diffraction System. A Cu K-Alpha radiation source was used. The experiments were analyzed at ambient conditions.

Analysis was performed on Compound A, Form II, as provided in Example 8. FIG. 6 shows peaks for Compound A, Form II, in the range of 2°-40° 2θ. FIG. 7 shows peaks for Compound A, Form II, in the range of 5°-40° 2θ. The X-ray powder diffraction pattern was generated to characterize Compound A, Form II, which exhibited reflections corresponding to d-spacings (±0.3° 2 theta) as shown in Table 3.

TABLE 3

| Position (° 2θ)(±0.3° 2θ) | d-spacing (Å) | Relative Intensity (%) |
|---|---|---|
| 3.33 | 26.56 | 100.0 |
| 6.61 | 13.38 | 8.2 |
| 9.92 | 8.91 | 1.4 |
| 13.23 | 6.69 | 5.4 |
| 16.51 | 5.37 | 7.0 |
| 17.16 | 5.17 | 33.7 |
| 17.41 | 5.09 | 18.0 |
| 17.82 | 4.98 | 6.1 |
| 18.25 | 4.86 | 9.8 |
| 19.03 | 4.66 | 3.6 |
| 19.80 | 4.48 | 4.7 |
| 20.75 | 4.28 | 17.2 |
| 21.06 | 4.22 | 12.9 |
| 21.53 | 4.13 | 16.5 |
| 22.10 | 4.02 | 4.4 |
| 22.74 | 3.91 | 4.9 |
| 23.50 | 3.78 | 3.4 |
| 23.85 | 3.73 | 4.4 |
| 24.42 | 3.65 | 3.7 |
| 26.44 | 3.37 | 2.3 |
| 27.61 | 3.23 | 3.7 |
| 28.09 | 3.18 | 13.5 |
| 28.52 | 3.13 | 10.1 |
| 30.29 | 2.95 | 4.8 |
| 30.70 | 2.91 | 3.9 |
| 31.84 | 2.81 | 3.3 |
| 32.24 | 2.78 | 1.4 |
| 33.17 | 2.70 | 2.2 |
| 33.58 | 2.67 | 3.0 |
| 34.61 | 2.59 | 4.6 |
| 36.38 | 2.47 | 2.1 |
| 37.83 | 2.38 | 1.3 |
| 39.27 | 2.29 | 1.8 |

Example 10: Solid-State NMR Characterization of Compound A, Form II

A sample of Compound A, Form II, was characterized by the respective carbon-13 and nitrogen-15 solid-state NMR (ssNMR) spectra. ssNMR carbon-13 and nitrogen-15 spectra were recorded on a Bruker AV500 NMR spectrometer operating at 125.757789 MHz and 50.677733 MHz, respectively, using a Bruker 4 mm H/F/X BB double resonance CPMAS probe. The spectra were collected utilizing proton to carbon-13 and proton to nitrogen-15 cross-polarization (CP) with contact times of 3 ms and 7 ms, respectively. A 100 kHz spin lock and an 83.3 kHz square contact pulse were used for CP on the proton channel. Linearly ramped contact pulses, starting at 50% and ending at 100% with respect to pulse power, with the respective power calibrated to produce maximum signal, were applied during cross-polarization on the carbon-13 and nitrogen-15 channels. Other experimental parameters used for data acquisition were a proton 90-degree pulse of 100 kHz, proton TPPM decoupling during acquisition at 100 kHz, and a pulse delay of 3.5 s. 4600 and 16000 scans for signal averaging were collected for the carbon-13 and nitrogen-15 spectra, respectively. Carbon-13 and nitrogen-15 spectra were acquired utilizing a magic-angle spinning (MAS) rate of 13 kHz. A Lorentzian line broadening of 30 Hz was applied to the carbon-13 and nitrogen-15 spectra before Fourier Transformation. Chemical shifts are reported on the TMS scale by using the carbonyl carbon and the amine nitrogen in glycine as secondary references. The carbonyl carbon was set to 176.70 ppm and the amine nitrogen was set to −346.40 ppm to reference the carbon-13 and nitrogen-15 CPMAS spectra, respectively.

Carbon-13 peaks are observed at 19.45, 20.14, 34.74, 63.16, 68.28, 70.83, 79.94, 85.97, 104.7, 128.15, 141.96, 154.39, and 176.28 ppm, and nitrogen-15 peaks are observed at −257.03, −255.06, −95.48 ppm. FIG. 8 and FIG. 9 show the carbon-13 and nitrogen-15 CPMAS spectra for Compound A, Form II, respectively. In the carbon-13 CPMAS spectrum, spinning sidebands are indicated by asterisks.

Example 11: Crystallization Experiments

Crystallization experiments were conducted in the solvent systems shown in Table 4. Typically, 400 μL solvent was pipetted into a 5-mL glass vial followed by addition of a sufficient amount of molnupiravir (MK-4482, EIDD-2801) to create a slurry. Vials were stirred at ambient temperature for 24 hr. Solid was isolated by centrifugation.

TABLE 4

| | |
|---|---|
| Ethanol | Slurry |
| 2-propanol | Slurry |
| Acetonitrile | Slurry |
| Water | Slurry |
| 1-propanol | Slurry |
| Acetone | Slurry |
| Acetone with 5% water | Evaporation |
| Acetone with 10% water | Evaporation |
| Acetonitrile with 10% water | Evaporation |
| Methanol | Slurry |
| Ethyl acetate | Slurry |
| THF | Slurry |
| MTBE | Slurry |
| Isopropyl acetate | Slurry |
| Toluene | Slurry |
| n-Heptane | Slurry |
| 2-Methyltetrahydrofuran | Slurry |
| 1% water in acetone/MTBE | Antisolvent |

XRPD (FIGS. 10A-D) and DSC (FIGS. 11A-F) analyses indicated that Compound A, Form I was obtained from each of the above crystallization experiments. DSC of the products all exhibited melting points of about 162° C. and heats of fusion of about 100 J/g. TGA thermograms did not show any significant weight loss for these crystals.

When THF was used as solvent in an experiment as described above, Compound A, THF Solvate was obtained. XRPD is FIG. 10E. Melting events at ~110° C. and ~162° C. were observed using DSC (FIG. 11C, top trace) and TGA showed a weight loss of about 8% weight loss around 80-100° C.

It will be appreciated that various of the above-discussed and other features and functions, or alternatives thereof, may be desirably combined into many other different systems or applications. Also, that various presently unforeseen or unanticipated alternatives, modifications, variations or improvements therein may be subsequently made by those skilled in the art that are also intended to be encompassed by the following claims.

What is claimed is:

1. Crystalline form of {(2R,3S,4R,5R)-3,4-dihydroxy-5-[(4Z)-4-(hydroxyimino)-2-oxo-3,4-dihydropyrimidin-1(2H)-yl]oxolan-2-yl}methyl 2-methylpropanoate, wherein said crystalline form is characterized by an X-ray powder diffraction pattern containing at least four ° 2θ values measured using CuKα radiation chosen from: about 3.34° 2θ, about 6.53° 2θ, about 13.11° 2θ, about 18.13° 2θ, about 19.51° 2θ, about 19.97° 2θ, and about 21.47° 2θ.

2. The crystalline form according to claim 1, wherein said crystalline form has a monoclinic crystal system.

3. The crystalline form according to claim 1, wherein said crystalline form is prepared by crystallization from ethyl acetate and MTBE.

4. The crystalline form according to claim 1, wherein said crystalline form is prepared by crystallization from acetone and n-heptane vapors.

5. The crystalline form according to claim 1, wherein said crystalline form is prepared by crystallization from water.

6. The crystalline form according to claim 1, characterized by an X-ray powder diffraction pattern containing ° 2 θ values measured using CuKα radiation at about 3.34° 2θ, about 19.51° 2θ, about 19.97° 2θ, and about 21.47° 2θ.

7. The crystalline form according to claim 1, characterized by having an X-ray powder diffraction containing at least five ° 2 θ values measured using CuKα radiation chosen from: about 3.34° 2θ, about 6.53° 2θ, about 13.11° 2θ, about 17.06° 2θ, about 17.33° 2θ, about 18.13° 2θ, about 19.51° 2θ, about 19.97° 2θ, and about 21.47° 2θ.

8. Crystalline form of {(2R,3S,4R,5R)-3,4-dihydroxy-5-[(4Z)-4-(hydroxyimino)-2-oxo-3,4-dihydropyrimidin-1(2H)-yl]oxolan-2-yl}methyl 2-methylpropanoate, wherein said crystalline form is characterized by an X-ray powder diffraction pattern containing (a) at least four ° 2θ values measured using CuKα radiation chosen from: about 3.33° 2θ, about 6.61° 2θ, about 9.92° 2θ, about 13.23° 2θ, about 16.51° 2θ, about 17.82° 2θ, about 19.03° 2θ, about 22.10° 2θ, and about 23.85° 2θ; or (b) at least four ° 2θ values measured using CuKα radiation chosen from: about 17.7° 2θ, about 18.2° 2θ, about 18.9° 2θ, about 21.0° 2θ, and about 22.0° 2θ.

9. The crystalline form according to claim 8, wherein said crystalline form is prepared by crystallization from acetone and n-heptane.

10. The crystalline form according to claim 8, characterized by an X-ray powder diffraction pattern containing ° 2θ values measured using CuKα radiation at: about 3.33° 2θ, about 17.82° 2θ, about 19.03° 2θ, and about 22.10° 2θ.

11. The crystalline form according to claim 8, characterized by an X-ray powder diffraction pattern containing at least five ° 2θ values measured using CuKα radiation chosen from: about 3.33° 2θ, about 6.61° 2θ, about 9.92° 2θ, about 13.23° 2θ, about 16.51° 2θ, about 17.82° 2θ, about 19.03° 2θ, about 22.10° 2θ, and about 23.85° 2θ.

12. A pharmaceutical composition comprising the crystalline form according to claim 1 and a pharmaceutically acceptable carrier.

13. The pharmaceutical composition according to claim 12, wherein the pharmaceutical composition is a solid dosage form for oral administration.

14. A pharmaceutical composition comprising the crystalline form according to claim 8 and a pharmaceutically acceptable carrier.

15. The pharmaceutical composition according to claim 14, wherein the pharmaceutical composition is a solid dosage form for oral administration.

16. A method of inducing an antiviral response in a subject in need thereof comprising administering the crystalline form according to claim 1 to the subject.

17. The method according to claim 16, wherein the subject has SARS-COV-2.

18. A method of inducing an antiviral response in a subject in need thereof comprising administering the crystalline form according to claim 8 to the subject.

19. The method according to claim 18, wherein the subject has SARS-COV-2.

* * * * *